(12) United States Patent
Takemura et al.

(10) Patent No.: US 6,573,260 B1
(45) Date of Patent: Jun. 3, 2003

(54) CYCLOALKYL-SUBSTITUTED AMINOMETHYLPYRROLIDINE DERIVATIVES

(75) Inventors: Makoto Takemura, Tokyo (JP); Hisashi Takahashi, Tokyo (JP); Rie Miyauchi, Tokyo (JP); Toshiyuki Takeda, Tokyo (JP); Isao Hayakawa, Tokyo (JP)

(73) Assignee: Daiichi Pharmaceutical Co., Ltd., Tokyo (JP)

(*) Notice: Subject to any disclaimer, the term of this patent is extended or adjusted under 35 U.S.C. 154(b) by 0 days.

(21) Appl. No.: 09/856,631
(22) PCT Filed: Nov. 22, 1999
(86) PCT No.: PCT/JP99/06521
§ 371 (c)(1), (2), (4) Date: May 24, 2001
(87) PCT Pub. No.: WO00/31062
PCT Pub. Date: Jun. 2, 2000

(30) Foreign Application Priority Data

Nov. 24, 1998 (JP) .......................................... 10-332235

(51) Int. Cl.$^7$ .................. A61K 31/4709; C07D 401/04
(52) U.S. Cl. .................... 514/230.2; 514/300; 514/312; 514/313; 514/314; 544/101; 546/123; 546/156
(58) Field of Search ......................... 544/101; 546/123; 546/156; 514/230.2, 300, 312, 314, 313

(56) References Cited

U.S. PATENT DOCUMENTS 6,329,391 B1 * 12/2001 Ledoussal et al. .......... 514/312

FOREIGN PATENT DOCUMENTS

| EP | 0341493 A | 11/1989 |
|---|---|---|
| JP | 10-287669 | 10/1998 |
| WO | 89/06649 | 7/1989 |
| WO | 92/09597 | 6/1992 |
| WO | WO 9639407 A | 12/1996 |

OTHER PUBLICATIONS

Ledoussal et al., Chemical Abstracts, vol. 136:20031, 2001.*
International Search Report (PCT/JP99/06521) 2000.

* cited by examiner

Primary Examiner—Richard L. Raymond
(74) Attorney, Agent, or Firm—Sughrue Mion, PLLC

(57) ABSTRACT

This invention provides a quinolone derivative which exerts strong antibacterial action upon various bacteria and has high safety, and it relates to a compound having a structure of formula (I), its salts and hydrates thereof:

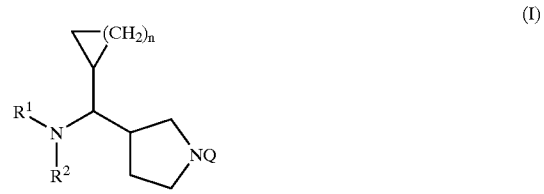

(I)

{$R^1$ and $R^2$: hydrogen, alkyl; n: 1 to 4; Q: following structure (Ia):

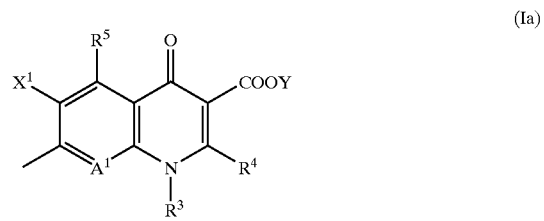

(Ia)

[$R^3$: alkyl, alkenyl, halogenoalkyl, cyclic alkyl, aryl, heteroaryl, alkoxyl, alkylamino; $R^4$: hydrogen, alkylthio; $R^5$: hydrogen, amino, hydroxyl, thiol, halogenomethyl, alkyl, alkenyl, alkynyl, alkoxyl; $X^1$: halogen, hydrogen, $A^1$: nitrogen, structure of formula (II):

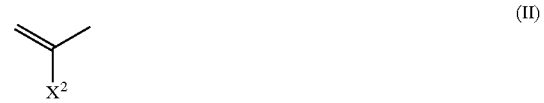

(II)

($X^2$: hydrogen, amino, halogen, cyano, halogenomethyl, halogenomethyl, alkyl, alkenyl, alkynyl, alkoxyl; $R^4$ and $R^3$ or $X^2$ and $R^3$ may together form a cyclic structure; Y: hydrogen, various ester forming groups]}.

17 Claims, No Drawings

CYCLOALKYL-SUBSTITUTED AMINOMETHYLPYRROLIDINE DERIVATIVES

TECHNICAL FIELD

This invention relates to a synthetic quinolone antibacterial agent useful as a drug for humans, animals or fishes or an antibacterial preservative.

This invention also relates to a synthetic quinolone antibacterial agent in which the structure of substituent at the 7 position of 1,4-dihydro-4-oxoquinoline skeleton or at the 10-position of 2,3-dihydro-7-oxo-7H-pyrido[1,2,3-de][1.4]benzoxazine skeleton exerts important influence upon the expression of pharmacological effects such as antibacterial activity, pharmacokinetics and safety, having a 3-[1-amino-1-cycloalkyl]methylpyrrolidin-1-yl group which can provide excellent antibacterial activity, pharmacokinetics and safety, as a substituent at the 7- or 10-position, and also having excellent antibacterial activity, proper pharmacokinetics and high safety, namely to a 6-fluoro-1-[2-(S)-fluoro-1-(R)-cyclopropyl]-1,4-dihydro-4-oxoquinoline-3-carboxylic acid derivative or a 2,3-dihydro-3-(S)-methyl-7-oxo-7H-pyrido[1,2,3-de][1.4]benzoxazine-6-carboxylic acid derivative, and to an antibacterial agent and an antibacterial preparation, which contain the compound.

BACKGROUND ART

Since the discovery of Norfloxacin, antibacterial activity and pharmacokinetics of synthetic quinolone antibacterial agents have been improved, and many compounds are now used in the clinical field as chemotherapeutic agents which are effective in almost systemic infectious diseases.

In recent years, generation of bacteria having low sensitivity to synthetic quinolone antibacterial agents has been increasing in the field of clinics. For example, like the case of Staphylococcus aureus (MRSA) and pneumococcus (PRSP) which are non-sensitive to β-lactam antibiotics and enterococcus (VRE) which is non-sensitive to aminoglycoside antibacterial agents, a case has been increasing in which a Gram-positive bacterium originally resistant to drugs other than synthetic quinolone antibacterial agents becomes low-sensitive to synthetic quinolone antibacterial agents too. In consequence, development of a drug having further high efficacy has been called for in the field of clinics. On the other hand, it has been revealed that synthetic quinolone antibacterial agents cause a side effect in which convulsion is induced when a non-steroidal anti-inflammatory drug is simultaneously used, as well as other side effects such as phototoxicity, so that development of a synthetic quinolone antibacterial agent having further high safety has also been called for in the field.

It is known that structures of substituents at the 7-position and 1-position have a great influence to the antibacterial activity, pharmcokinetics and safety of synthetic quinolone antibacterial agents. It is already known that quinolone derivatives having 3-aminamethylpyrrolidine as a substituent show strong antibacterial activity for Gram-negative and Gram-positive bacteria. For example, a 7-(3-ainomethylpyrrolidin-1-yl)quinolonecarboxylic acid derivative is described in *Journal of Medicinal Chemistry*, vol. 29, p. 445 (1986), a 7-[3-(1-amino-1-methylethyl)pyrrolidin-1-yl)quinolonecarboxylic acid derivative is described in *Journal of Medicinal Chemistry*, vol. 37, p. 733 (1994), and a 7-[3-(1-aminoalkyl)pyrrolidin-1-yl]quinolonecarboxylic acid derivative is described in *Chemical & Pharmaceutical Bulletin*, vol. 42, p. 1442 (1994). However, no compounds are known which have a 3-(1-amino-1-cycloalkyl)methylpyridin-1-yl group at the 7-position and are also related to the present invention.

On the other hand, quinolone derivatives having 3-aminomethylpyrrolidine as a substituent are compounds which show strong antibacterial activity, but, since most of these compounds have low selective toxicity, they act upon not only bacteria but also eucaryotic cells so that it is difficult to use them as medical drugs or animal drugs.

Also, it is known that quinolone derivatives having a 3-aminopyrrolidine derivative at the 7-position and 2-(S)-fluoro-1-(R)-cyclopropyl group at the 1-position of the quinoline skeleton have weaker micronucleus inducing toxicity than those corresponding 1-cyclopropylquinolone derivatives. Their examples are described in *Journal of Medicinal Chemistry*, vol. 37. P. 3344 (1994).

On the other hand, quinolonecarboxylic acid derivatives having a 3-[1-amino-1-cycloalkyl]methylpyrrolidin-1-yl group as a substituent, which are related to the present invention, are exemplified for example in JP-W-3-502452 (the term "JP-W" as used herein means an "unexamined published Japanese international patent application"), and it describes compounds represented by a formula (a) or (b) shown below. However, substituent at the 5-position of these exemplified quinolones is limited to a straight, branched or cyclic lower alkyl having 1 to 3 carbon atoms, and JP-W-3-502452 does not describe compounds having the 1-[2-(S)-fluoro-1-(R)-cyclopropyl]quinoline skeleton or 3-(S)-methyl-7H-pyrido[1,2,3-de][1.4]benzoxazine skeleton related to the present invention. In addition, JP-W-3-502452 does not disclose illustrative examples of the 3-[1-amino-1-cycloalkyl]methylpyrrolidin-1-yl group.

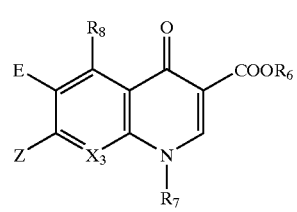

Formula (a)

[In the above formula, $R_7$ is an alkyl having 1 to 4 carbon atoms, a vinyl, a haloalkyl, a hydroxyalkyl having 2 to 4 carbon atoms, a cycloalkyl having 3 to 6 carbon atoms, a phenyl or a phenyl substituted with a halogen, an alkyl, $NH_2$ or OH, $R_6$ is a straight, branched or cyclic lower alkyl having 1 to 3 carbon atoms, and $X_3$ is CH, CF, CCl, CBr, N, $CCF_3$, $CNH_2$, $CNO_2$, CR or COR' (in these formulae, R is a lower alkyl and R' is hydrogen or a lower alkyl). Definitions of substituents of the compound of formula (a) are independent to those the compound of the present invention.]

In the above formula, Z is a group represented by the following formula (b).

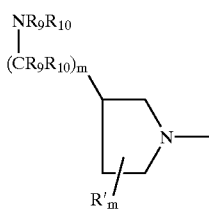

Formula (b)

(In this formula, m is an integer of from 0 to 4, and the substituents $R_9$ and $R_{10}$ are each independently a hydrogen atom, a lower alkyl or a cycloalkyl. Definitions of substituents of the compound of formula (b) are independent to those the compound of the present invention.)

In addition, PCT WO 96/39407 discloses compounds represented by the following formula (c), but they are limited to 2-pyridone derivatives such as 4H-4-oxoquinotozone skeleton, and PCT WO 96/39407 does not describe compounds having the 1,4-dihydro-4-oxoquinoline skeleton or 2,3-dihydro-3-(S)-ethyl-7-oxo-7H-pyrido[1,2,3-de][1.4]benzoxazine skeleton related to the present invention. Also, PCT WO 96/39407 does not disclose illustrative examples of optically active 3-[1-amino-1-cyclopropyl] methylpyrrolidin-1-yl group.

In addition, PCT WO 96/39407 does not describe about safety of the compounds of formula (c).

Formula (c)

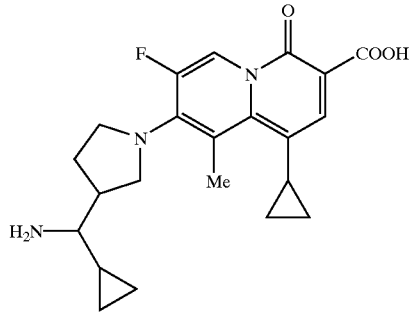

DISCLOSURE OF INVENTION

In view of the above, the inventors of the present invention have conducted intensive studies with the aim of providing the field of clinics with a compound which has excellent antibacterial activity, high efficacy and excellent safety. As a result of the extensive investigation, it has been found absolutely unexpectedly that a cycloalkyl-substituted aminomethylpyrrolidine derivative represented by the formula (I) described below, its salts and hydrates thereof can show strong antibacterial activity upon broad range of Gram-negative and Gram-positive bacteria, can show particularly strong antibacterial activity upon resistant strains of Gram-positive bacteria including MRSA, PRSP and VRE, and also have excellent safety and good pharmacokinetics, thereby resulting in the accomplishment of the present invention.

Particularly, it has been found that a compound represented by the following formula (I) in which a cycloalkyl-substituted aminomethylpyrrolidine derivative is introduced at the 7position of the 1[2-(S)-fluoro-1-(R)-cyclopropyl] quinoline skeleton, its salts and hydrates thereof show broad and excellent antibacterial activity upon any one of Gram-negative and Gram-positive bacteria including drug-resistant strains, have excellent safety with sharply attenuated micronucleus induction action, and also have excellent pharmacokinetics.

Accordingly, the present invention relates to a compound represented by the following formula (I), its salts and hydrates thereof:

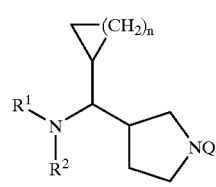

(I)

{wherein $R^1$ and $R^2$ each independently represents a hydrogen atom or an alkyl group having 1 to 6 carbon atoms, in which the alkyl group may have one or more substituents selected from the group consisting of a hydroxyl group, a halogen atom, an alkylthio group having 1 to 6 carbon atoms and an alkyloxy group; n is an integer of 1 to 4; and Q is a partial structure represented by the following formula (Ia):

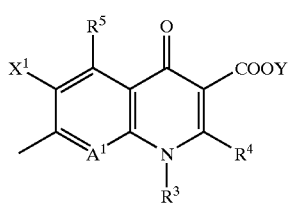

(Ia)

[wherein $R^3$ represents an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms which may have a substituent, an aryl group which may have a substituent, a heteroaryl group which may have a substituent, an alkoxyl group having 1 to 6 carbon atoms or an alkylamino group having 1 to 6 carbon atoms;

$R^4$ represents a hydrogen atom or an alkylthio group having 1 to 6 carbon atoms;

$R^4$ and the aforementioned $R^3$ may form together with a part of the mother skeleton a ring structure optionally containing a sulfur atom as a ring constituting atom thereof and optionally having an alkyl group having 1 to 6 carbon atoms as a substituent;

$R^5$ represents a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, in which the amino group may have one or more substituents selected from the group consisting of formyl group, an alkyl group having 1 to 6 carbon atoms and an acyl group having 2 to 5 carbon atoms;

$X^1$ represents a halogen atom or a hydrogen atom, $A^1$ represents a nitrogen atom or a partial structure represented by formula (II):

(wherein $x^2$ represents a hydrogen atom, an amino group, a halogen atom, a cyano group, a halogenomethyl group, a halogenamethoxyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, in which the amino group may have one or more substituents selected from the group consisting of a formyl group, an alkyl group having 1 to 6 carbon atoms and an acyl group having 2 to 5 carbon atoms; and $X^2$ and the aforementioned $R^3$ may form together with a part of the mother skeleton a ring structure optionally containing an oxygen atom, a nitrogen atom or a sulfur atom as a ring constituting atom thereof and optionally having an alkyl group having 1 to 6 carbon atoms as a substituent); and Y represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms or a phenylalkyl group composed of an alkylene group having 1 to 6 carbon atoms and a phenyl group]}.

The present invention also relates to each of the following items.

A compound, its salts and hydrates thereof, wherein Q in the formula (I) is a 6-caxboxy-9-fluoro-2,3-dihydro-3-(S)-methyl-7-oxo-7H-pyrido[1,2,3-de][1.4]benzoxazin-10-yl group;

the aforementioned compound, its salts and hydrates thereof, wherein the compound of formula (I) is a stereochemically pure compound;

the aforementioned compound, its salts and hydrates thereof, wherein $R^3$ in the formula (I) is a halogenocyclopropyl group;

the aforementioned compound, its salts and hydrates thereof, wherein the halogenocyclopropyl group in the formula (I) is a 1,2-cis-halogenocyclopropyl group;

the aforementioned compound, its salts and hydrates thereof, wherein the halogenocyclopropyl group in the formula (I) is a stereochemically pure substituent;

the aforementioned compound, its salts and hydrates thereof, wherein the halogenocyclopropyl group in the formula (I) is a (1R,2S)-2-halogenocyclopropyl group;

the aforementioned compound, its salts and hydrates thereof, wherein the halogen atom of the halogenocyclopropyl group in the formula (I) is a fluorine atom;

the aforementioned compound, its salts and hydrates thereof, wherein the compound of formula (I) is a stereochemically pure compound;

the aforementioned compound, its salts and hydrates thereof, wherein n in the formula (I) is 1;

the aforementioned compound, its salts and hydrates thereof, wherein the compound of formula (I) is a stereochemically pure compound;

7-[3-[1-(S)-amino-1-cyclopropyl]methylpyrrolidin-1-yl]-6-fluoro-1-[2-(S)-fluoro-1-(R)-cyclopropyl]-1,4-dihydro-8-methoxy-4-oxoquinoline-3-carboxylic acid, its salts and hydrates thereof; 5-amino-7-[3-[1-(S)-amino-1-cyclopropyl]methylpyrrolidin-1-yl]-6-fluoro-1-[2-(S)-fluoro-1-(R)-cyclopropyl]-1,4-dihydro-8-methyl-4-oxoquinoline-3-carboxylic acid, its salts and hydrates thereof;

5-amino-7-[3-[1-(S)-amino-1-cyclopropyl]methylpyrrolidin-1-yl]-6,8-difluoro-1-[2-(S)-fluoro-1-(R)-cyclopropyl]-1,4-dihydro-4-oxoquinoline-3-carboxylic acid, its salts and hydrates thereof; the aforementioned compound, its salts and hydrates thereof, wherein Y is a hydrogen atom;

a drug containing the aforementioned compound, its salts and hydrates thereof as an active ingredient; and an antibacterial agent containing the aforementioned compound, its salts and hydrates thereof as an active ingredient.

EMBODIMENT FOR CARRYING OUT INVENTION

Each of the substituents of the compound of the present invention represented by formula (I):

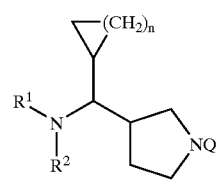

(wherein $R^1$, $R^2$, n and Q are as defined in the foregoing) will be explained in the following.

The substituents $R^1$ and $R^2$ is each independently a hydrogen atom or an alkyl group having 1 to 6 carbon atoms, wherein the alkyl group may have one or more substituents selected from the group consisting of a hydroxyl group, a halogen atom, an alkylthio group having 1 to 6 carbon atoms and an alkyloxy group.

The alkyl group may be either straight or branched group having 1 to 6 carbon atoms, and the preferred examples thereof are methyl, ethyl, normal propyl and isopropyl groups.

When the alkyl group has a hydroxyl group as a substituent, the alkyl group may be either straight or branched form having 1 to 6 carbon atoms, and the hydroxyl group may preferably be substituted on the terminal carbon atom of the alkyl group. Preferred examples of the allyl group having a hydroxyl group include those which have 1 to 3 carbon atoms, such as a hydroxymethyl group, a 2-hydroxyethyl group, a 2-hydroxypropyl group and a 3-hydroxypropyl group.

When the alkyl group has a halogen atom as a substituent, the alkyl group may be either straight or branched form having 1 to 6 carbon atoms, and a fluorine atom is desirable as the halogen atom. With regard to the number of fluorine atoms, it may be any one of from mono-substitution to perfluoro substitution. The examples thereof are monofluoromethyl, difluoromethyl, trifluoromethyl, 2-fluoroethyl, 2,2-difluoroethyl and 2,2,2-trifluoroethyl groups. Among these groups, a monofluoromethyl group and a 2-fluoroethyl group are more preferred.

When the alkyl group has an alkylthio group as a substituent, the alkyl group may be either straight or branched form having 1 to 6 carbon atoms, and the alkylthio group may also be either straight or branched form having 1 to 6 carbon atoms. An alkylthiomethyl group, an alkylthioethyl group and an alkylthiopropyl group are desirable as the alkyl group having an alkylthio group, and the alkylthio group may preferably have 1 to 3 carbon atoms. More preferred examples are a methylthiomethyl group, an ethylthiomethyl group and a methylthioethyl group.

When the alkyl group has an alkoxyl group as a substituent, the alkyl group may be either straight or branched form having 1 to 6 carbon atoms, and the alkoxyl group may also be either straight or branched form having 1 to 6 carbon atoms. An alkoxymethyl group, an alkoxyethyl group and an alkoxypropyl group are desirable as the alkyl group having an alkoxyl group, and the alkoxyl group may preferably have up to 3 carbon atoms. More preferred examples thereof are a methoxymethyl group, an ethoxymethyl group and a methoxyethyl group.

The symbol n is an integer of from 1 to 4, preferably 1 or 2, and more preferably 1.

Q is a partial structure represented by the following formula (Ia).

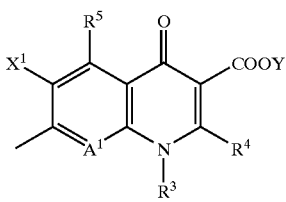

(Ia)

In the above formula (Ia), $R^3$ is an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms which may have a substituent, an aryl group which may have a substituent, a heteroaryl group which may have a substituent, an alkoxyl group having 1 to 6 carbon atoms or an alkylamino group having 1 to 6 carbon atoms.

In this case, an ethyl group is particularly desirable as the alkyl group having 1 to 6 carbon atoms. As the alkenyl group having 2 to 6 carbon atoms, a vinyl group or a 1-isopropenyl group is desirable. A 2-fluoroethyl group is desirable as the halogenoalkyl group having 1 to 6 carbon atoms. A cyclopropyl group is particularly desirable as the cyclic alkyl group, and a halogen atom, particularly a fluorine atom, is desirable as the substituent of the cyclic alkyl group.

Examples of the aryl group which may have a substituent are a phenyl group which may have 1 to 3 substituents selected from the group consisting for example of fluorine, chlorine, bromine or the like halogen atom, a hydroxyl group, an amino group, a nitro group, an alkyl group having 1 to 6 carbon atoms and an alkoxyl group having 1 to 6 carbon atoms, and its preferred illustrative examples are a phenyl group, a 2-fluorophenyl group, a 4-fluorophenyl group, a 2,4-difluorophenyl group, a 2-fluoro-4-hydroxyphenyl group, a 3-amino-4,6-difluorophenyl group and a 4,6-difluoro-3 methylaminophenyl group.

The heteroaryl group is a compound derived from a five or six-membered aromatic heterocyclic compound which contains one or more hetero atoms selected from a nitrogen atom, an oxygen atom and a sulfur atom. Examples thereof are a pyridyl group and a pyrimidyl group. As the substituent on these rings, an alkyl group, a halogen atom or the like is desirable. Particularly preferred is a 5-amino-2,4-difluoropyridyl group.

A methoxyl group is desirable as the alkoxyl group having 1 to 6 carbon atoms. A methylamino group is desirable as the alkylamino group having 1 to 6 carbon atoms.

As the substituent $R^3$, a cyclic alkyl group or a halogenocycloalkyl group is desirable. Among these groups, a cyclopropyl group or a 2-halogenocyclopropyl group is particularly desirable. As the halogen atom, a fluorine atom is desirable.

The substituent $R^4$ is a hydrogen atom or an alkylthio group having 1 to 6 carbon atoms, or $R^3$ and $R^4$ may together form a ring structure by incorporating a part of the mother skeleton (namely by including the nitrogen atom to which $R^3$ is bonded and the carbon atom to which $R^4$ is bonded). The thus formed ring may contain a sulfur atom as its constituting atom, and the ring may further have an alkyl group having 1 to 6 carbon atoms as a substituent. The ring to be formed herein may have a size of from four-membered ring to six-membered ring, and the ring may be saturated or unsaturated.

The substituent $X^1$ is a halogen atom or a hydrogen atom, and a fluorine atom is desirable in the case of the halogen atom. Among these atoms, a fluorine atom or a hydrogen atom is desirable as the substituent.

The substituent $R^5$ is a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, wherein the amino group may have one or two substituents selected from the group consisting of a formyl group, an alkyl group having 1 to 6 carbon atoms and an acyl group having 2 to 6 carbon atoms.

The alkyl group may be either straight or branched group having 1 to 6 carbon atoms, and its preferred examples are a methyl group, an ethyl group, a normal propyl group and an isopropyl group. The alkenyl group may be either straight or branched group having 2 to 6 carbon atoms and is preferably a vinyl group. The alkynyl group may be either straight or branched group having 2 to 6 carbon atoms and is preferably an ethynyl group. A fluorine atom is particularly desirable as the halogen of the halogenomethyl group, and its number may be from 1 to 3. The alkoxyl group may have 1 to 6 carbon atoms and is preferably a methoxyl group.

The substituent $^5$ is preferably a hydrogen atom, an alkyl group or an amino group, of which a methyl group or an unsubstituted amino group is more preferred.

When the substituent $R^5$ is an amino group, a hydroxyl group or a thiol group, these groups may be protected with ordinally used protective groups.

Examples of such protective groups include tert-butoxycarbonyl, 2,2,2-trichloroethoxycarbonyl and the like alkoxycarbonyl groups, benzyloxycarbonyl, para-methoxybenzyloxycarbonyl, para-nitrobenzyloxycarbonyl and the like aralkyloxycarbonyl groups, acetyl, methoxyacetyl, trifluoroacetyl, chloroacetyl, pivaloyl, formyl, benzoyl and the like acyl groups, tert-butyl, benzyl, para-nitrobenzyl, para-methoxybenzyl, triphenylmethyl and the like alkyl or aralkyl groups, methoxymethyl, tert-butoxymethyl, tetrahydropyranyl, 2,2,2-trichloroethoxymethyl and the like ethers and trimethylsilyl, isopropyldimethylsilyl, tert-butyldimethylsilyl, tribenzylsilyl, tert-butyldiphenylsilyl and the like substituted silyl groups. Compounds whose substituents are protected with these protective groups are particularly useful as production intermediates.

When $A^1$ is a partial structure represented by formula (II):

(II)

$X^2$ is a hydrogen atom, an amino group, a halogen atom, a cyano group, a halogenomethyl group, a halogenomethoxyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, wherein the amino group may have one or two substituents selected from the group consisting of a formyl group, an alkyl group having 1 to 6 carbon atoms and an acyl group having 2 to 5 carbon atoms.

The alkyl group may be either straight or branched group having 1 to 6 carbon atoms and the preferred examples thereof are a methyl group, an ethyl group, a normal propyl group and an isopropyl group. The alkenyl group may be either straight or branched group having 2 to 6 carbon atoms and is preferably a vinyl group. The alkynyl group may be either straight or branched group having 2 to 6 carbon atoms and is preferably an ethynyl group. A fluorine atom is particularly desirable as the halogen of the halogenomethyl group, and its number may be from 1 to 3. The alkoxyl group may have 1 to 6 carbon atoms and is preferably methoxyl group. A fluorine atom is particularly desirable as the halogen of the halogenamethoxyl group, and its number may be from 1 to 3.

Among these substituents, a halogen atom, an alkyl group or an alkoxyl group is desirable, and a fluorine atom, a methyl group or a methoxyl group is more desirable. These substituents are particularly desirable in the case where Q is the partial structure represented by the formula (Ia).

In addition, $X^2$ and the aforementioned $R^3$ may together form a hydrocarbon ring structure (size of the ring may be from four-membered ring to seven-membered ring, and the ring may be saturated or unsaturated) by incorporating a part of the mother skeleton (namely by including the carbon atom to which $X^2$ is bonded and the nitrogen atom to which $R^3$ is bonded), and the thus formed ring may contain an oxygen atom, a nitrogen atom or a sulfur atom as its constituting atom, and the ring may also have an alkyl group having 1 to 6 carbon atoms as a substituent.

The partial structure represented by the aforementioned formula (Ia) is desirable as Q. In this case, it is desirable that $A^1$ is the partial structure of formula (II).

When Q is the partial structure of formula (Ia) and $A^1$ is the partial structure of the formula (II), a preferred combination of $R^5$ and $X^2$ is a case in which $R^5$ is an amino group, a hydrogen atom, a hydroxyl group or an alkyl group having 1 to 6 carbon atoms and $X^2$ is a halogen atom, an alkyl group having 1 to 6 carbon atoms, an alkoxyl group having 1 to 6 carbon atoms, a halogenomethoxyl group or a hydrogen atom.

A more preferred combination is a case in which $R^5$ is an amino group, a hydrogen atom, a hydroxyl group or a methyl group and $X^2$ is a fluorine atom, a methyl group, a methoxyl group, a difluoramethoxyl group or a hydrogen atom.

A most preferred combination is a case in which $R^5$ is an amino group, a hydrogen atom, a hydroxyl group or a methyl group and $X^2$ is a fluorine atom, a methyl group or a methoxyl group. For these $R^5$ and $X^2$ groups, a fluorine atom is desirable as $X^1$.

When the substituents $X^1$ and $X^2$ are halogen atoms, $X^1$ is particularly preferably a fluorine atom and $X^2$ is preferably a fluorine atom or a chlorine atom.

Next, the halogenocyclopropyl group of $R^3$ will be explained.

As the substitutable halogen atom, a fluorine atom and a chlorine atom can be exemplified, of which a fluorine atom is particularly preferred.

Regarding the steric environment at this moiety, it is particularly desirable that the halogen atom and pyridonecarboxylic acid moiety take cis-configuration on the cyclopropane ring.

So-called enantiomorphic isomers are present due to the cis-2-halogenocyclopropyl moiety alone of $R^3$, and strong antibacterial activity and high safety have been found in both isomers.

The compound of the present invention shows excellent characteristics by having a substituent represented by the following formula at the 10-position of the 2,3-dihydro-3-(S)-methyl-7-oxo-7H-pyrido[1,2,3-de][1.4]benzoxazine-6-carboxylic acid skeleton or at the 7-position of the 6-fluoro-1-[2-(S)-fluoro-1-(R)-cyclopropyl]-1,4-dihydro-4-oxoquinoline-3-carboxylic acid skeleton.

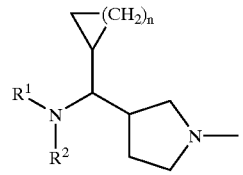

This substituent exists in the following four optical isomeric forms, due to the asymmetric carbon atom at 3-position of the pyrrolidine ring and the asymmetric carbon atom at 1-position of the cycloalkyl-substituted aminomethyl substituent.

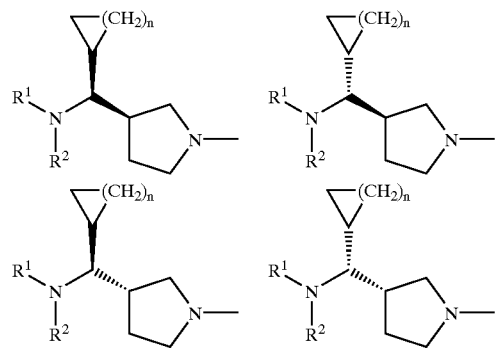

Among these, the present inventors considered that the structure of the following formula was more desirable.

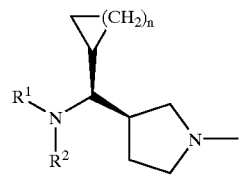

That is, it was revealed that, when the 10-position of the 2,3-dihydro-3-(S)-methyl-7-oxo-7H-pyrido[1,2,3-de][1.4] benzoxazine-6-carboxylic acid skeleton or the 7-position of the 6-fluoro-1-[2-(S)-fluoro-1-(R)-cyclopropyl]-1,4-dihydro-4-oxoquinoline-3-carboxylic acid skeleton has the substituent represented by the above formula, the compound of the present invention shows strong antibacterial activity upon Gram-negative bacteria and Gram-positive bacteria and also shows excellent safety and good pharmacokinetics, such as negativness of the micronuclear test (very weak micronucleus induction toxicity) which was not expected before the present invention.

Where the compound of formula (I) of the present invention has a structure allowing the existence of diastereomers, it is desirable to administer a compound comprising a pure diastereomer in administration to humans or animals. The term "comprising a pure diastereomer" as used herein means not only a case in which it is completely free from the other diastereomer(s) but also a case in which it is in a chemically pure degree. In other words, it is interpretable that the other diastereomer(s) may be present in such a degree that it does not exert influences upon physical constants and physiological activities of the compound.

Also, the term "stereochemically pure" as used herein means a compound consisting of one of its stereoiomers when the compound has a plurality of isomers due to asymmetric carbon atom (s) contained therein. The term "pure" in this case can also be considered in the same manner as described above.

The compound of the present invention may be used either in its free form or as an acid addition salt or a salt of its carboxyl group. Examples of the acid addition salt include hydrochloride, sulfate, nitrate, hydrobromide, hydroiodide, phosphate and the like inorganic acid salts, or methanesulfonate, benzenesulfonate, toluenesulfonate (sulfonate), acetate, citrate, maleate, fumarate, lactate (carboxylate) and the like organic acid salts.

The salt of carboxyl group may be either inorganic or organic salt, and its illustrative examples include lithium salt, sodium salt, potassium salt and the like alkali metal salts, magnesium salt, calcium salt and the like alkaline earth metal salts, ammonium salt, or triethylamine salt, N-methylglucamine salt, tris-(hydroxylmethyl) aminomethane salt and the like.

Also, these free form, acid addition salts and salts of carboxyl group of the compound may be present as hydrates.

When the compound of the present invention is used for antibacterial purpose, it is desirable to use a carboxylic acid compound in which the group Y is a hydrogen atom, while a quinolone derivative whose carboxylic acid moiety is an ester is useful as a synthesis intermediate or a prodrug. For example, alkyl esters, benzyl esters, alkoxyalkyl esters, phenylalkyl esters and phenyl esters are useful as synthesis intermediates.

Also, the ester to be used as a prodrug is an ester which is susceptible to an in vivo cleavage to form a free carboxylic acid, and its illustrative examples include acetoxymethyl ester, pivaloyloxymethyl ester, ethoxycarbonyl ester, choline ester, dimethylaminoethyl ester, 5-indanyl ester, phthalidinyl ester, 5-alkyl-2-oxo-1,3-dioxol-4-ylmethyl ester, and oxoalkyl ester such as 3-acetoxy-2-oxobutyl eater.

The compound of the present invention represented by the formula (I) can be produced by various method, and, in a preferred example of these methods, it can be produced for example by reacting a compound represented by formula (III):

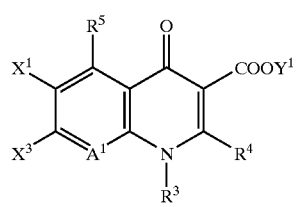

[wherein $X^3$ is a substituent which functions as a leaving group, such as a fluorine atom, a chlorine atom, a bromine atom, a substituted or unsubstituted phenylsulfonyl group or a substituted or unsubstituted alkylsulfonyl group having 1 to 3 carbon atoms, $Y^1$ is the Y defined in the formula (I) or a boron-containing group represented by formula (IV):

$$-B(Y^{11})Y^{12} \quad (IV)$$

(wherein $Y^{11}$ and $Y^{12}$ each represents a fluorine atom or an alkylcarbonyloxy group having 2 to 4 carbon atoms), and $R^3, R^4, R^5, A^1$ and $X^1$ are as defined in the formula (I)] with a compound represented by formula (V):

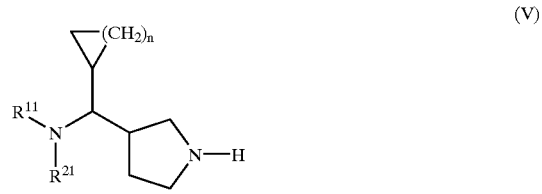

[wherein $R^{11}$ and $R^{21}$ each independently represents a hydrogen atom, an alkyl group having 1 to 6 carbon atoms or a protective group for amino group, in which the alkyl group may have a substituent selected from the group consisting of a hydroxyl group, a halogen atom, an alkylthio group having 1 to 6 carbon atoms and an alkoxyl group having 1 to 6 carbon atoms, and n is as defined in the formula (I)] or an addition salt thereof (examples of the acid addition salt include hydrochloride, sulfate, nitrate, hydrobromide, hydroiodide, phosphate and the like inorganic acid salts, or methanesulfonate, benzenesulfonate, toluenesulfonate (sulfonate), acetate, citrate, maleate, fumarate, lactate (carboxylate) and the like organic acid salts).

The reaction can be carried out using or without using a solvent. The solvent to be used in the reaction may be any solvent which is inert under the reaction conditions, and its illustrative examples include dimethyl sulfoxide, pyridine, acetonitrile, ethanol, chloroform, dimethylformamide, dimethylacetamide, N-methylpyrrolidone, tetrahydrofuran, water and 3-methoxybutanol or a mixture thereof.

Preferably, the reaction may be carried out in the presence of an acid acceptor such as an inorganic base (e.g., an alkali metal or alkaline earth metal carbonate or bicarbonate) or an organic base (e.g., triethylamine, pyridine, 1,8-diazabicycloundecene).

The reaction can be carried out at a temperature of from room temperature to 200° C., preferably from 25 to 150° C. The reaction is carried out for a period of from 30 minutes to 48 hours and completes generally after about 30 minutes to 2 hours.

When the amino group is protected, examples of the protective group for amino group include those which are generally used in this field, such as tert-butoxycarbonyl, 2,2,2-trichloroethoxycarbonyl and the like alkoxycarbonyl groups, benzyloxycarbonyl, para-methoxybenzyloxycarbonyl, para-nitrobenzyloxycarbonyl and the like aralkyloxycarbonyl groups, acetyl, methoxyacetyl, trifluoroacetyl, chloroacetyl, pivaloyl, formyl, benzoyl and the like acyl groups, tert-butyl, benzyl, para-nitrobenzyl, para-methoxybenzyl, triphenylmethyl and the like alkyl or aralkyl groups, methoxymethyl, tert-butoxymethyl, tetrahydropyranyl, 2,2,2-trichloroethoxymethyl and the like ethers and trimethylsilyl, isopropyldimethylsilyl, tert-butyldimethylsilyl, tribenzylsilyl, tert-butyldiphenylsilyl and the like substituted silyl groups.

When Y and $Y^1$ are an alkyl group having 1 to 6 carbon atoms, an alkoxymethyl group having 2 to 7 carbon atoms or a phenylalkyl group composed of an alkylene group having 1 to 6 carbon atoms and phenyl group, the compound of interest can be converted into its corresponding carboxylic acid compound by treating it under an acidic or basic condition which is generally employed for the hydrolysis of carboxylic acid esters.

When $Y^1$ is a structure of the formula (IV), its conversion into corresponding carboxylic acid compound can be effected by allowing the compound (III) to react with the compound (V) and then treating it under an acidic or basic condition.

In addition, when de-protection is necessary, the compound of interest represented by the formula (I) can be obtained by removing the protective group under suitable conditions for the protective group.

The compound of formula (V) can be produced by various methods, and, though not particularly limited, it can be synthesized by a method shown in the reference examples as a preferred example in which synthesis of 3-[1-(S)-amino-1-cycloalkyl]methylpyrrolidine is described as a synthetic example of 3-[1-amino-1-cycloalkyl]methylpyrrolidine, so that the compound of formula (V) can be produced in accordance with this method using a known optically active cycloalkyl-substituted glycine derivative.

The cis-2-fluorocyclopropylamine comprised of a pure isomer, which is desirable for the synthesis of the compound of formula (I) comprised of a pure isomer, can be synthesized for example by the method described in JP-A-2-231475 (the term "JP-A" as used herein means an "unexamined published Japanese patent application"). Synthesis of the compound of formula (I) comprised of a pure isomer can be carried out using the thus obtained optically active cis-2-fluorocyclopropylamine derivative as the material, in accordance with the method described for example in JP-A-2-231475.

The following can be cited as illustrative examples of the compound of the present invention.

10-[3-(R)-[1-(S)-Amino-1-cyclopropyl]methylpyrrolidine-1-yl]-9-fluoro-2,3-dihydro-3-(S)-methyl-7-oxo-7H-pyrido[1,2,3-de][1.4]benzoxazine-6-carboxylic acid;

8-amino-10-[3-(R)-[1-(S)-amino-1-cyclopropyl] methylpyrrolidine-1-yl]-9-fluoro-2,3-dihydro-3-(S)-methyl-7-oxo-7H-pyrido[1,2,3-de][1.4]benzoxazine-6-carboxylic acid;

7-[3-(R)-[1-(S)-amino-1-cyclopropyl]methylpyrrolidin-1-yl]-6-fluoro-1-[2-(S)-fluoro-1-(R)-cyclopropyl]-1,4-dihydro-8methoxy-4-oxoquinoline-3-carboxylic acid;

5-amino-7-[3-(R)-[1-(S)-amino-1-cyclopropyl] methylpyrrolidin-1-yl]6-fluoro-1-[2-(S)-fluoro-1-(R)-cyclopropyl]-1,4-dihydro-8-methoxy-4-oxoquinoline-3-carboxylic acid;

7-[3-(R)-[1-(S)-amino-1-cyclopropyl]methylpyrrolidin-1-yl]-6-fluoro-1-[2-(S)-fluoro-1-(R)-cyclopropyl]-1,4-dihydro-8-methyl-4-oxoquinoline-3-carboxylic acid;

5-amino-7-[3-(R)-[1-(S)-amino-1-cyclopropyl] methylpyrrolidin-1-yl]-6,8-difluoro-1-[2-(S)-fluoro-1-(R)-cyclopropyl]-1,4-dihydro-4-oxoquinoline-3-carboxylic acid; and 5-amino-7-[3-(R)-[1-(S)-cyclopropyl-1-N-methylamino] methylpyrrolidin-1-yl]-6,8-difluoro-1-[2-(S)-fluoro-1-(R)-cyclopropyl]-1,4-dihydro-4-oxoquinoline-3-carboxylic acid.

These compounds have the following structures.

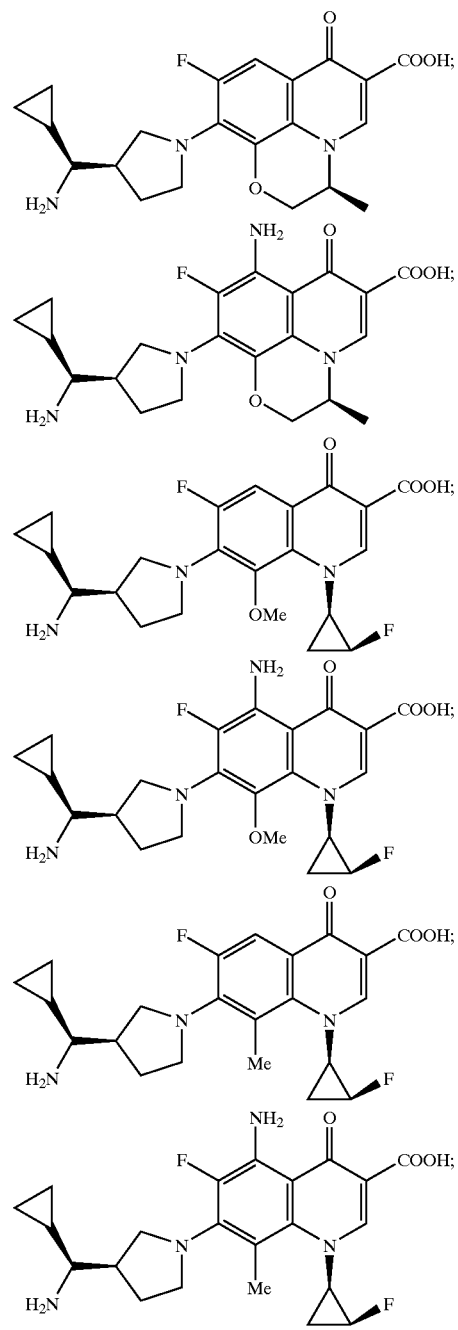

-continued

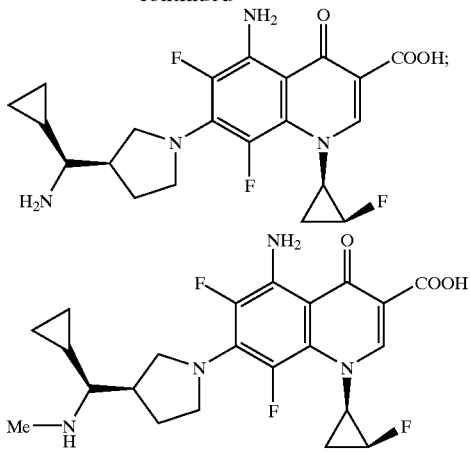

Since the compound of the present invention has strong antibacterial actions, it can be used as drugs for use in human bodies, animals and fishes or as preservatives of agricultural chemicals and food.

When the compound of the present invention is used as a drug for human bodies, its dose is within the range of from 50 mg to 1 g, preferably from 100 mg to 300 mg, per day for an adult.

Its dose as a drug for use in animals varies depending on the purpose of its administration (treatment or prevention), kind and size of each animal to be treated and kind and degree of each infected pathogenic bacterium, but the dose may be within the range of generally from 1 mg to 200 mg, preferably from 5 mg to 100 mg, per 1 kg body weight per day.

The daily dose may be used once a day or by dividing it into 2 to 4 doses per day. As occasion demands, the daily dose may exceed the aforementioned range.

Since the compound of the present invention is active against a broad range of microorganisms causing various infectious diseases and effective to treat, prevent or alleviate diseases induced by these pathogens.

Illustrative examples of bacteria and bacterioid microorganisms on which the compound of the present invention is effective include those which belong to the genus Staphylococcus, *Streptococcus pyogenes, hemolytic streptococci*, enterococcus, pneumococcus, those which belong to the genus Peptostreptococcus, *Neisseria gonorrhoeae, Escherichia coli*, those which belong to the genera Citrobacter and Shigella, *Klebsiella pneumoniae*, those which belong to the genera Enterobacter, Serratia and Proteus, *Pseudomonas aeruginosa, Haemophilus influenzae*, those which belong to the genera Acinetobacter and Campylobacter and *Chlamydia trachomatis*. Illustrative examples of diseases which are induced by these pathogens include folliculitis, furuncle, carbuncle, erysipelas, phlegmon, lymphangitis/lymphadenitis, felon, subcutaneous abscess, hidradenitis, acne conglobata, infectious atheroma, perirectal abscess, mastitis, superficial secondary infections after injury, burn injury, operative wound and the like, pharyngitis, acute bronchitis, tonsilitis, chronic bronchitis, bronchiectasis, diffuse bronchiolitis, secondary infection of chronic respiratory disease, pneumonia, pyelonephritis, cystitis, prostatitis, epididymitis, gonococcal urethritis, non-specific urethritis, cholecystitis, cholangitis, bacillary dysentery, enteritis, uterine adnexitis, intrauterine infection, bartholinitis, blepharitis, hordeolum, dacryocystitis, tarsadenitis, corneal ulcer, octitis media, sinusitis, periodentitis, pericoronitis, jaw infection, peritonitis, endocarditis, sepsis, meningitis and skin infection.

The compound of the present invention is also effective against various microorganisms causing infectious diseases in animals, such as those which belong to the genera Escherichia, Salmonella, Pasteurella, Haemaphilus, Bordetella, Staphylococcus and Mycoplasma. Illustrative examples of such diseases include colibacillosis, pullorum disease, avian paratyphoid, avian cholera, infectious coryza, staphylococcosis, mycoplasma infection and the like in the case of birds; colibacillosis, salmonellosis, pasteurellosis, haemophilus infection, atrophic rhinitis, exudative epidermis, mycoplasma infection and the like in the case of pigs; colibacillosis, salmonellosis, hemorrhagic sepsis, mycoplasma infection, bovine pleuropneumonia, bovine mastitis and the like in the case of cattle; colisepsis, salmonella infection, hemorrhagic sepsis, uterine empyema, cystitis and the like in the case of dogs; and exudative pleurisy, cystitis, chronic rhinitis, haemophilus infection, kitten diarrhea, mycoplasma infection and the like in the case of cats.

The antibacterial preparation which comprises the compound of the present invention can be prepared by selecting an appropriate preparation depending on each administration method and employing generally used various preparation method. Regarding the dosage form of the antibacterial preparation which uses the compound of the present invention as its principal agent, tablets, powders, granules, capsules, solutions, syrups, elixirs, oily or aqueous suspensions and the like can be exemplified as oral preparations.

Regarding injections, a stabilizing agent, an antiseptic agent and a solubilizing agent may be used in the preparation, or a solution which may contain these auxiliary agents may be contained in a container and made into a solid preparation by freeze-drying or the like means to be re-dissolved when used. In addition, a single dose may be contained in a single container or multiple doses may be contained in the same container.

Also, solutions, suspensions, emulsions, ointments, gels, creams, lotions, sprays and the like can be exemplified as preparations for external use.

Solid preparations may contain pharmaceutically acceptable additives together with the active compound and can be prepared for example by mixing the compound with additives optionally selected from fillers, extenders, binders, disintegrators, solubilization enhancing agents, moistening agents, lubricating agents and the like. As liquid preparations, solutions, suspensions, emulsions and the like can be exemplified, which may contain a suspending agent, an emulsifying agent and the like as additives.

Examples of the method for administering the compound of the present invention to animals include a method in which it is orally administered directly or by mixing it with feed, a method in which it is made into a solution and then orally administered directly or by mixing it with drinking water or feed and a method in which it is administered by injection.

Regarding the pharmaceutical preparations for use in the administration of the compound of the present invention to animals, it can be made optionally into powders, fine subtilaes, soluble powders, syrups, solutions or injections making use of the techniques generally used in this field.

Formulation examples of the pharmaceutical preparations are shown below.

Formulation Example 1 (Capsules)

| | |
|---|---:|
| Compound of Inventive Example 2 | 100.0 mg |
| Corn starch | 23.0 mg |
| CMC calcium | 22.5 mg |
| Hydroxymethyl cellulose | 3.0 mg |
| Magnesium stearate | 1.5 mg |
| Total | 150.0 mg |

Formulation Example 2 (Solutions)

| | |
|---|---:|
| Compound of Inventive Example 2 | 1–10 g |
| Acetic acid or sodium hydroxide | 0.5–2 g |
| Ethyl para-hydroxybenzoate | 0.1 g |
| Purified water | 88.9–98.4 g |
| Total | 100 g |

Formulation Example 3 (Powders for Mixing With Feed)

| | |
|---|---:|
| Compound of Inventive Example 2 | 1–10 g |
| Corn starch | 98.5–89.5 g |
| Light anhydrous silicic acid | 0.5 g |
| Total | 100 g |

BEST MODE FOR CARRYING OUT INVENTION

Examples of the present invention are given below by way of illustration and not by way of limitation.

REFERENCE EXAMPLE 1

1-Cyclopropyl-2-propen-1-one

Under a stream of nitrogen, cyclopropylmethyl ketone (6.33 g, 75.2 mmol) was dissolved in anhydrous tetrahydrofuran (75 ml). While stirring under ice-cooling, to this was added dropwise a solution which had been prepared by dissolving N-methylanilinium trifluoroacetate (25.0 g, 113 .mol) in 37% formaldehyde aqueous solution (10.2 ml) under ice-cooling. After the dropwise addition, the reaction solution was heated under reflux for 7 hours. After cooling, the reaction solution was mixed with diethyl ether (100 ml) and stirred, and then the organic layer was separated. The aqueous layer was extracted with diethyl ether (50 ml). The organic layers were combined, gradually mixed with saturated sodium bicarbonate aqueous solution (100 ml) and stirred, and then the organic layer was separated. The thus separated organic layer was washed with saturated sodium chloride aqueous solution (100 ml). This was dried over anhydrous magnesium sulfate, filtered and then concentrated to 8.01 g under a reduced pressure of 150 mmHg, thereby obtaining a yellow oil containing the title compound. This product was used in the subsequent reaction without purification.

$^1$H-NMR (400 MHz, CDCl$_3$) δ: 0.90–0.96 (2H, m), 1.08–1.13 (2H, m), 2.14–2.25 (1H, m), 5.82 (1H, dd, J=10.74, 1.47 Hz), 6.29 (1H, dd, J=17.57, 1.47 Hz), 6.47 (1H, dd, J=17.57, 10.74 Hz)

REFERENCE EXAMPLE 2

Cyclopropyl[1-[1-(R)-phenylethyl]pyrrolidin-3-yl] ketone

The product containing 1-cyclopropyl-2-propen-1-one described in Reference Example 1 (8.01 g) and N-(normal-butoxymethyl)-N-[1-(R)-phenylethyl] trimethylsilylmethylamine (23.2 g, 79.9 mmol) were dissolved in dry dichloroethane (350 ml) to which was subsequently added dropwise trifluoroacetic acid (500 μl). After 12 hours of stirring at room temperature, the reaction solution was washed with saturated sodium bicarbonate aqueous solution (100 ml) and saturated sodium chloride aqueous solution (100 ml) in that order. This was dried over anhydrous magnesium sulfate, filtered and then concentrated under a reduced pressure. The resulting residue was applied to a flash silica gel chromatography and eluted with n-hexane:ethyl acetate=2:1, thereby obtaining 9.08 g (49.6%) of the title compound as a colorless oil. In this connection, this product was obtained as a 1:1 diastereomer mixture.

$^1$H-NMR (400 MHz, CDCl$_3$) 67 : 0.83–0.88 (2H, m), 0.99–1.02 (2H, m), 1.38 (3H×1/2, d, J=2.93 Hz), 1.40 (3H x×1/2, d, J=2.44 Hz), 1.62–1.76 (1H, m), 1.90–2.17 (2H, m), 2.35–2.93 (4H, m), 3.22–3.26 (2H, m), 7.23–7.34 (5H, m)

REFERENCE EXAMPLE 3

3-[1-(tert-Butoxycarbonyl)amino-1-cyclopropyl] methyl-1-[1-(R)-phenylethyl]pyrrolidine Cyclopropyl[1-[1-(R)-phenylethyl]pyrrolidin-3-yl] ketone (1.563 g, 7.793 mmol) was dissolved in anhydrous methanol (25 ml). To this were added ammonium acetate (5.236 g, 67.93 mmol), sodium cyanoborohydride (435.2 mg, 6.925 mmol) and Molecular Sieves 4A powder (1.86 g), and the mixture was stirred at room temperature for 16 hours under a stream of nitrogen. The reaction solution was filtered through celite, and the solvent was evaporated under a reduced pressure. The resulting residue was dissolved in dichloromethane (100 ml), and the solution was washed with saturated sodium bicarbonate aqueous solution (50 ml) and saturated sodium chloride aqueous solution (50 ml) in that order, and then dried over anhydrous magnesium sulfate. After filtration, the solvent was concentrated under a reduced pressure. The thus obtained residue was dissolved in dry dichloromethane (25 ml) to which, under ice-cooling, was subsequently added dropwise dichloromethane (5 ml) solution of di-tert-butyl bicarbonate (2.225 g, 10.19 mmol). The reaction solution was stirred at room temperature for 2 hours and then concentrated under a reduced pressure. The thus obtained residue was applied to a flash silica gel chromatography and eluted with chloroform:methanol= 10:1, thereby obtaining 1.299 g (55.5%) of the title compound as a colorless oil. In this connection, this product was obtained as a mixture of four optical isomers.

$^1$H-NMR (400 MHz, CDCl$_3$) 67 : 0.20–0.30, 0.35–0.52, 0.68–0.78 (4H, m), 1.36 (3H×1/4, d, J=5.86 Hz), 1.39 (3H×3/4, d, J=5.86 Hz), 1.43 (9H×1/4, s), 1.45 (9H×3/4, s), 1.61–1.74 (1H, m), 2.25–2.76, 2.80–3.07, 3.18–3.26 (9H, m), 5.28 (1H, brs), 7.23–7.34 (5H, m)

REFERENCE EXAMPLE 4

1-Benzyloxycarbonyl-3-[1-(tert-butoxycarbonyl) amino-1-cyclopropyl]methylpyrrolidine (F1, F2, F3 and F4)

3-[1-(tert-Butoxycarbonyl)amino-1-cyclopropyl]methyl-1-[1-(R)-phenylethyl]pyrrolidine (1.234 g, 3.582 mmol) was dissolved in dry dichloromethane (20 ml) to which, under ice-cooling, was subsequently added dropwise benzyl chloroformate (1278 μl, 8.955 mmol). After 8 hours of stirring at room temperature, the reaction solution was concentrated under a reduced pressure. The thus obtained residue was applied to a flash silica gel chromatography and eluted with n-hexane:ethyl acetate=2:1, thereby obtaining 959 mg (71.5%) of the title compound as a colorless oil.

Thereafter, this product was subjected to fractional HPLC using a chiral column to isolate and purify four optical isomers F1, F2, F3 and F4.

HPLC fractionation conditions;

Column: CHIRALPAKAD (Daicel Chemical Industries), 2 cm×25 cm

Mobile phase: n-hexane:2-propanol=80:20 (v/v)

Flow rate: 5.0 ml/min

Temperature: room temperature

Detection: UV (254 nm)

Retention time of each optical isomer

F1: 18 minutes; F2: 23 minutes; F3: 26 minutes; F4: 30 minutes

Isomer F1: colorless amorphous, 229 mg (17.0%);
$^1$H-NMR (400 MHz, CDCl$_3$) δ: 0.27–0.32 (2H, m), 0.41–0.45 (1H, m), 0.54–0.61 (1H, m), 0.72–0.79 (1H, m), 1.43 (9H, s), 1.66–1.78 (1H, m), 1.99–2.08 (1H, m), 2.30–2.36 (1H, m), 2.90–3.03 (1H, m), 3.12–3.26 (1H, m), 3.28–3.36 (1H, m), 3.49–3.72 (2H, m), 4.50 (1H, brs), 5.13 (2H, s), 7.30–7.37 (5H, m)

Isomer F2: colorless amorphous, 96 mg (7.2%);
$^1$H-NMR (400 MHz, CDCl$_3$) δ: 0.29–0.37 (2H, m), 0.40–0.45 (1H, m), 0.57–0.62 (1H, m), 0.76–0.79 (1H, m), 1.43 (9H, s), 1.68–1.78 (1H, m), 2.04–2.09 (1H, m), 2.36–2.40 (1H, m), 2.95–3.09 (1H, m), 3.16 (1H, t, J=10.74 Hz), 3.31–3.39 (1H, m), 3.54–3.68 (2H, m), 4.47 (1H, brs), 5.13 (2H, s), 7.29–7.37 (5H, m)

Isomer F3: colorless amorphous, 140 mg (10.4%);
$^1$H-NMR (400 MHz, CDCl$_3$) δ: 0.27–0.39 (2H, m), 0.41–0.45 (1H, m), 0.54–0.62 (1H, m), 0.72–0.80 (1H, m), 1.43 (9H, s), 1.66–1.79 (1H, m), 2.04–2.09 (1H, m), 2.37–2.40 (1H, m), 2.95–3.08 (1H, m), 3.16 (1H, t, J=10.74 Hz), 3.32–3.39 (1H, m), 3.54–3.68 (2H, m), 4.48 (1H, brs), 5.13 (2H, s), 7.30–7.37 (5H, m)

Isomer F4: colorless amorphous, 296 mg (22.1%);
$^1$H-NMR (400 MHz, CDCl$_3$) δ: 0.27–0.33 (2H, m), 0.41–0.45 (1H, m), 0.54–0.62 (1H, m), 0.72–0.80 (1H, m), 1.43 (9H, s), 1.68–1.78 (1H, m), 1.99–2.09 (1H, m), 2.29–2.39 (1H, m), 2.90–3.03 (1H, m), 3.12–3.26 (1H, m), 3.28–3.37 (1H, m), 3.49–3.73 (2H, m), 4.50 (1H, brs), 5.13 (2H, s), 7.30–7.37 (5H, m)

Based on the results of the analysis of these $^1$H-NMR data, it was confirmed that each combination of F1 and F4 and F2 and F3 has the enantiomorphic relation.

INVENTIVE EXAMPLE 1

5-Amino-7-[3-(1-amino-1-cyclopropyl)
methylpyrrolidin-1-yl]-6,8-difluoro-1-[2-(S)-fluoro-
1-(R)-cyclopropyl]-1,4-dihydro-4-oxoquinoline-3-
carboxylic acid (the substituent at the 7-position is
originated from F1)

1-Benzyloxy carbonyl-3-[1-(tert-butoxycarbonyl)amino-1-cyclopropyl]methylpyrrolidine (originated from F1 of Reference Example 4; 185 mg, 0.494 mmol) was dissolved in anhydrous methanol (30 ml), and the solution was mixed with 10% palladium on carbon catalyst (water content 50%, 200 mg) and stirred at room temperature for 1 hour in an atmosphere of hydrogen under atmospheric pressure. After filtration of the reaction solution through celite, the resulting filtrate was concentrated under a reduced pressure. The thus obtained residue and triethylamine (2 ml) were added to dry acetonitrile (10 ml), and the mixture was further mixed with 5-amino-6,7,8-trifluoro-1-[2-(S)-fluoro-1-(R)-cyclopropyl]-1,4-dihydro-4-oxoquinoline-3-carboxylic acid (130 mg, 0.412 mmol) and heated under reflux for 16 hours. After cooling of the reaction solution, the thus precipitated crystals were collected by filtration, washed with acetonitrile, mixed with concentrated hydrochloric acid (10 ml) under ice-cooling and then stirred at room temperature for 5 minutes. This was mixed with distilled water (15 ml), and the thus obtained acidic aqueous solution was washed with dichloromethane (20 ml×2), adjusted to pH 11 with sodium hydroxide aqueous solution under ice-cooling and then washed with chloroform (10 ml). The resulting basic aqueous solution was adjusted to pH 7.4 with 1 N hydrochloric acid and extracted with chloroform (100 ml×4). After drying over anhydrous sodium sulfate, the solvent was evaporated under a reduced pressure. Thereafter, the resulting residue was purified by recrystallizing from ethanol-28% aqueous ammonia and then dried under a reduced pressure, thereby obtaining 160 mg (88.9%) of the title compound as yellow needle crystals.

$^1$H-NMR (400 MHz, 0.1 N NaOD) δ: 0.11–0.18 (2H, m), 0.39 (2H, d, J=7.81 Hz), 0.57–0.67 (1H, m), 1.24–1.35 (1H, m), 1.43–1.61 (3H, m), 1.93–2.06 (2H, m), 3.20–3.26 (1H, m), 3.37–3.49 (2H, m), 3.59–3.72 (2H, m), 4.97 (1H, dm, J=64.16 Hz), 8.21 (1H, s)

Melting point: 185–193° C.

Elemental analysis data for $C_{21}H_{23}F_3N_4O_3 \cdot 0.25H_2O$
Calcd.: C, 57.20; H, 5.37; N, 12.71. Found: C, 57.16; H, 5.39; N, 12.88.

INVENTIVE EXAMPLE 2

5-Amino-7-[3-(1-amino-1-cyclopropyl)
methylpyrrolidin-1-yl]-6,8-difluoro-1-[2-(S)-fluoro-
1-(R)-cyclopropyl]-1,4-dihydro-4-oxoquinoline-3-
carboxylic acid (the substituent at the 7-position is
originated from F2)

1-Benzyloxycarbonyl-3-[1-(tert-butoxycarbonyl)amino-1-cyclopropyl]methylpyrrolidine (originated from F2 of Reference Example 4; 75 mg, 0.200 mmol) was dissolved in anhydrous methanol (15 ml), and the solution was mixed with 10% palladium on carbon catalyst (water content 50%, 100 mg) and stirred at room temperature for 1 hour in an atmosphere of hydrogen under atmospheric pressure. After filtration of the reaction solution through celite, the resulting filtrate was concentrated under a reduced pressure. The thus obtained residue and triethylamine (1 ml) were added to dry acetonitrile (5 ml), and the mixture was further mixed with 5-amino-6,7,8-trifluoro-1-[2-(S)-fluoro-1-(R)-cyclopropyl]-1,4-dihydro-4-oxoquinoline-3-carboxylic acid (53 mg, 0.167 mmol) and heated under reflux for 12 hours. After cooling of the reaction solution, the thus precipitated crystals were collected by filtration, washed with acetonitrile, mixed with concentrated hydrochloric acid (5 ml) under ice-cooling and then stirred at room temperature for 5 minutes. This was mixed with distilled water (10 ml), and the thus obtained acidic aqueous solution was washed with dichloromethane (15 ml×2), adjusted to pH 11 with sodium hydroxide aqueous solution under ice-cooling and then washed with chloroform (10 ml). The resulting basic aqueous solution was adjusted to pH 7.4 with 1 N hydrochloric acid and extracted with chloroform (80 ml×3). After drying over anhydrous sodium sulfate, the solvent was evaporated under a reduced pressure. Thereafter, the resulting residue was purified by recrystallizing from ethanol-28% aqueous ammonia and then dried under a reduced pressure, thereby obtaining 55 mg (75.5%) of the title compound as yellow needle crystals.

$^1$H-NMR (400 MHz, 0.1 N NaOD) δ: 0.13–0.19 (1H, m), 0.22–0.30 (1H, m), 0.41–0.49 (1H, m), 0.52–0.60 (1H, m), 0.73–0.84 (1H, m), 1.53–1.72 (3H, m), 1.86 (1H, t, J=9.28 Hz), 2.11–2.29 (2H, m), 3.44–3.57 (2H, m), 3.62–3.68 (1H, m), 3.72–3.95 (2H, m), 4.96 (1H, dm, J=63.95 Hz), 8.24 (1H, s)

Melting point: 190–192° C.

Elemental Analysis data for $C_{21}H_{23}F_3N_4O_3 \cdot 0.25H_2O$ Calcd.: C, 57.20; H, 5.37; N, 12.71. Found: C, 57.27; H, 5.36; N, 12.65.

INVENTIVE EXAMPLE 3

5-Amino-7-[3-(1-amino-1-cyclopropyl) methylpyrrolidin-1-yl]-6,8-difluoro-1-[2-(S)-fluoro-1-(R)-cyclopropyl]-1,4-dihydro-4-oxoquinoline-3-carboxylic acid (the substituent at the 7-position is originated from F3)

1-Benzyloxycarbonyl-3-[1-(tert-butoxycarbonyl)amino-1-cyclopropyl]methylpyrrolidine (originated from F3 of Reference Example 4; 100 mg, 0.267 mmol) was dissolved in anhydrous methanol (20 ml), and the solution was mixed with 10% palladium on carbon catalyst (water content 50%, 100 mg) and stirred at room temperature for 1 hour in an atmosphere of hydrogen under atmospheric pressure. After filtration of the reaction solution through celite, the resulting filtrate was concentrated under a reduced pressure. The thus obtained residue and triethylamine (2 ml) were added to dry acetonitrile (8 ml), and the mixture was further mixed with 5-amino-6,7,8-trifluoro-1-[2-(S)-fluoro-1-(R)-cyclopropyl]-1,4-dihydro-4-oxoquinoline-3-carboxylic acid (80 mg, 0.222 mmol) and heated under reflux for 16 hours. After cooling of the reaction solution, the thus precipitated crystals were collected by filtration, washed with acetonitrile, mixed with concentrated hydrochloric acid (10 ml) under ice-cooling and then stirred at room temperature for 5 minutes. This was mixed with distilled water (15 ml), and the thus obtained acidic aqueous solution was washed with dichloromethane (20 ml×2), adjusted to pH 11 with sodium hydroxide aqueous solution under ice-cooling and then washed with chloroform (20 ml). The resulting basic aqueous solution was adjusted to pH 7.4 with 1 N hydrochloric acid and extracted with chloroform (80 ml×4). After drying over anhydrous sodium sulfate, the solvent was evaporated under a reduced pressure. Thereafter, the resulting residue was purified by recrystallizing from ethanol-28% aqueous ammonia and then dried under a reduced pressure, thereby obtaining 59 mg (60.8%) of the title compound as yellow needle crystals.

$^1$H-NMR (400 MHz, 0.1 N NaOD) δ: 0.12–0.17 (1H, m), 0.21–0.28 (1H, m), 0.41–0.48 (1H, m), 0.51–0.60 (1H, m), 0.72–0.82 (1H, m), 1.44–1.53 (3H, m), 1.81 (1H, t, J=8.79 Hz), 2.09–2.28 (2H, m), 3.41–3.47 (1H, m), 3.49–3.57 (1H, m), 3.59–3.66 (1H, m), 3.72–3.80 (2H, m), 4.95 (1H, dm, J=65.11 Hz), 8.19 (1H, s)

Melting point: 193–194° C.

Elemental analysis data for $C_{21}H_{23}F_3N_4O_3 \cdot 0.25H_2O$ Calcd.: C, 57.20; H, 5.37; N, 12.71. Found: C, 57.21; H, 5.37; N, 12.70.

INVENTIVE EXAMPLE 4

5-Amino-7-[3-(1-amino-1-cyclopropyl) methylpyrrolidin-1-yl]-6,8-difluoro-1-[2-(S)-fluoro-1-(R)-cyclopropyl]-1,4-dihydro-4-oxoquinoline-3-carboxylic acid (the substituent at the 7-position is originated from F4)

1-Benzyloxycarbonyl-3-[1-(tert-butoxycarbonyl)amino-1-cyclopropyl]methylpyrrolidine (originated from F4 of Reference Example 4; 200 mg, 0.534 mmol) was dissolved in anhydrous methanol (20 ml), and the solution was mixed with 10% palladium on carbon catalyst (water content 50%, 200 mg) and stirred at room temperature for 1 hour in an atmosphere of hydrogen under atmospheric pressure. After filtration of the reaction solution through celite, the resulting filtrate was concentrated under a reduced pressure. The thus obtained residue and triethylamine (3 ml) were added to dry acetonitrile (15 ml), and the mixture was further mixed with 5-amino-6,7,8-trifluoro-1-[2-(S)-fluoro-1-(R)-cyclopropyl]-1,4-dihydro-4-oxoquinoline-3-carboxylic acid (141 mg, 0.445 mmol) and heated under reflux for 16 hours. After cooling of the reaction solution, the thus precipitated crystals were collected by filtration, washed with acetonitrile, mixed with concentrated hydrochloric acid (10 ml) under ice-cooling and then stirred at room temperature for 5 minutes. This was mixed with distilled water (20 ml), and the thus obtained acidic aqueous solution was washed with dichloromethane (20 ml×2), adjusted to pH 11 with sodium hydroxide aqueous solution under ice-cooling and then washed with chloroform (20 ml). The resulting basic aqueous solution was adjusted to pH 7.4 with 1 N hydrochloric acid and extracted with chloroform (100 ml×4). After drying over anhydrous sodium sulfate, the solvent was evaporated under a reduced pressure. Thereafter, the resulting residue was purified by recrystallizing from ethanol-28% aqueous ammonia and then dried under a reduced pressure, thereby obtaining 138 mg (71.1%) of the title compound as yellow needle crystals.

$^1$H-NMR (400 MHz, 0.1 N NaOD) δ: 0.12–0.23 (2H, m), 0.41–0.51 (2H, m), 0.70–0.87 (1H, m), 1.46–1.66 (3H, m), 1.80–1.88 (1H, m), 2.08–2.30 (2H, m), 3.46–3.60 (2H, m), 3.62–3.69 (1H, m), 3.72–3.82 (2H, m), 4.96 (1H, dm, J=63.89 Hz), 8.19 (1H, s)

Melting point: 188–194° C.

Elemental analysis data for $C_{21}H_{23}F_3N_4O_3$ Calcd.: C, 57.79; H, 5.31; N, 12.84. Found: C, 57.56; H, 5.39; N, 12.88.

REFERENCE EXAMPLE 5

Ethyl 4-(S)-benzyloxycarbonylamino-4-cyclopropyl-3-oxobutanoate

Malonic acid monoethyl ester (988.4 mg, 7.482 mmol) was dissolved in anhydrous tetrahydrofuran (20 ml), and the solution was mixed with magnesium ethoxide (488 mg, 3.93 mmol) under ice-cooling and then stirred at room temperature for 2 hours. The reaction solution was concentrated to dryness under a reduced pressure, and the thus obtained powder was dissolved in anhydrous tetrahydrofuran (30 ml).

L-N-Benzyloxycarbonyl-cyclopropylglycine (1.332 g, 5.334 mmol) was dissolved in anhydrous tetrahydrofuran (20 ml), and the solution was mixed with N,N'-carbonyldiimidazole (910 mg, 5.61 mmol) under ice-cooling and then stirred at room temperature for 2 hours. Under ice-cooling, the aforementioned tetrahydrofuran solution previously prepared was added dropwise to the just prepared solution, and the mixture was stirred at room temperature for 16 hours.

The reaction solution was concentrated under a reduced pressure, and the resulting residue was mixed with toluene (60 ml) and 10% citric acid aqueous solution (50 ml) and stirred at room temperature for 5 minutes. The organic layer was separated and the aqueous layer was extracted with toluene (20 ml×2). The organic layers were combined, washed with water (50 ml) and saturated sodium chloride aqueous solution (50 ml) in that order, and then dried over anhydrous magnesium sulfate. After filtration, the solvent was evaporated under a reduced pressure and the resulting residue was applied to a flash silica gel chromatography and eluted with n-hexane:ethyl acetate=2:1, thereby obtaining 1.527 g (89.4%) of the title compound as a colorless oil.

$^1$H-NMR (400 MHz, CDCl$_3$) δ: 0.53–0.61 (3H, m), 0.67–0.77 (1H, m), 0.90–1.01 (1H, m), 1.27 (3H, t, J=7.33 Hz), 3.65 (2H, s), 3.89–3.93 (1H, m), 4.20 (2H, q, J=7.33 Hz), 5.10 (2H, s), 5.47 (1H, brs), 7.31–7.35 (5H, m)

REFERENCE EXAMPLE 6

Ethyl 4-(S)-benzyloxycarbonylamino-4-cyclopropyl-3-hydroxybutanoate

Ethyl 4-(S)-benzyloxycarbonylamino-4-cyclopropyl-3-oxobutanoate (1.526 g, 4.778 mmol) was dissolved in anhydrous ethanol (15 ml), and the solution was mixed with sodium borohydride (94.6 mg, 2.50 mmol)under ice-cooling and stirred at the same temperature for 1 hour. Under ice-cooling, the reaction solution was mixed with water (20 ml) and then ethanol was evaporated under a reduced pressure. The thus obtained residue was mixed with chloroform (50 ml) and stirred, and then the thus separated chloroform layer was washed with saturated sodium chloride aqueous solution (30 ml) and dried over anhydrous magnesium sulfate. After filtration, the solvent was evaporated to dryness under a reduced pressure, thereby obtaining 1.509 g (98.3%) of the title compound as a colorless oil. This product was used in the subsequent reaction without purification.

$^1$H-NMR (400 MHz, CDCl$_3$) δ: 0.24–0.67 (4H, m), 0.96–1.06 and 1.08–1.16 (total 1 H, m for each), 1.27 (3H, t, J=7.32 Hz), 2.45–2.58 (1H, m), 2.66–2.73 (1H, m), 2.84–3.01 (1H, m), 3.33 (1H, brs), 4.17 (2H, q, J=7.32 Hz), 5.09 (2H, s), 5.18 and 5.28 (total 1H, br-s for each), 7.30–7.37 (5H, m)

REFERENCE EXAMPLE 7

Ethyl 4-(S)-benzyloxycarbonylamino-4-cyclopropyl-2-butenoate

Ethyl 4-(S)-benzyloxycarbonylamino-4-cyclopropyl-3-hydroxybutanoate (1.488 g, 4.630 mmol) was dissolved in dry dichloromethane (50 ml) and stirred at -15° C. while adding triethylamine (1,291 μl, 9.260 mmol), and then methanesulfonyl chloride (449 μl, 5.80 mmol) was added dropwise thereto and the mixture was stirred at the same temperature for 1 hour. 1,8-Diazabicyclo[5.4.0]-7-undecene (1,486 μl, 1.955 mmol) was added dropwise to the reaction solution, and the mixture was gradually warmed up to room temperature and then stirred for 15 hours. The reaction solution was washed with 10% citric acid aqueous solution (50 ml), and the organic layer was separated and then the aqueous layer was extracted with chloroform (30 ml). The organic layers were combined, washed with water (50 ml) and saturated sodium chloride aqueous solution (50 ml) in that order, and then dried over anhydrous magnesium sulfate. After filtration, the solvent was evaporated under a reduced pressure, and the thus obtained residue was applied to a flash silica gel chromatography and eluted with n-hexane:ethyl acetate=4:1, thereby obtaining 1.174 g (87.2%) of the title compound as a light yellow oil.

$^1$H-NMR (400 MHz, CDCl$_3$) δ: 0.31–0.37 (1H, m), 0.39–0.48 (1H, m), 0.52–0.65 (1H, m), 0.86–0.95 (1H, m), 1.29 (3H, t, J=7.33 Hz), 3.73 (1H, brs), 4.20 (2H, q, J=7.33 Hz), 4.92 (1H, brs), 5.11 (2H, s), 5.97 (1H, d, J=15.63 Hz), 6.91 (1H, dd, J=15.63, 5.37 Hz), 7.31–7.36 (5H, m)

REFERENCE EXAMPLE 8

Ethyl 4-(S)-benzyloxycarbonylamino-4-cyclopropyl-3-nitromethylbutanoate

Ethyl 4-(S)-benzyloxycarbonylamino-4-cyclopropyl-2-butenoate was dissolved in dry nitromethane (15 ml), and the solution was mixed with 1,1,3,3-tetramethylguanidine (133 μl, 1.05 mol) and stirred at room temperature for 17 hours. The reaction solution was concentrated under a reduced pressure, the resulting residue was dissolved in chloroform (50 ml), and the solution was washed with 10% citric acid aqueous solution (50 ml) and saturated sodium chloride aqueous solution (50 ml) in that order, and then dried over anhydrous magnesium sulfate, thereby obtaining 1.207 g (96.1%) of the title compound as a yellow oil. This product (diastereomer mixture) was used in the subsequent reaction without purification.

$^1$H-NMR (400 MHz, CDCl$_3$) δ: 0.31–0.45 (1H, m), 0.48–0.56 (1H, m), 0.61–0.70 (1H, m), 0.82–0.92 (1H, m), 1.26 (3H, t, J=7.33 Hz), 2.49 (d, J=7.32 Hz), 2.53 (d, J=6.34 Hz), 2.67 (d, J=5.72 Hz), 2.71 (d, J=5.86 Hz), (2.49, 2.53, 2.67, 2.67, total 1 H), 3.00 (1H, q, J=6.34 Hz), 3.13 (1H, q, J=7.32 Hz), 4.15 (2H, q, J=7.33 Hz), 4.57 and 4.59 (total 2 H, d, J=7.33 Hz), 4.86 (1H, br-s), 5.10 (2H, s), 7.31–7.36 (5H, m)

REFERENCE EXAMPLE 9

4-(1-(S)-tert-Butoxycarbonylamino-1-cyclopropyl]methylpyrrolidin-2-one (isomer A)

Ethyl 4-(S)-benzyloxycarbonylamino-4-cyclopropyl-3-nitromethylbutanoate (16.4 g, 41.0 mmol) was dissolved in ethanol (500 ml), and the solution was mixed with 10% palladium on carbon catalyst (water content 50%, 16 g) and subjected to 5 hours of catalytic hydrogenation at room temperature. After removal of the catalyst by celite filtration, the resulting filtrate was heated under reflux for 6 hours. The solvent was evaporated under a reduced pressure, the resulting residue was dissolved in dry dichloranethane, the resulting solution was mixed with triethylamine (8.24 ml, 59.1 mmol) and then with di-tert-butyl bicarbonate (11.32 ml, 49.2 mmol), and then the mixture was stirred at room temperature for 6 hours. After concentration of the reaction solution under a reduced pressure, the thus obtained residue was applied to a flash silica gel chromatography and eluted with chloroform:methanol=95:5, and the thus obtained crystals were purified by recrystallizing them from a chloroform-n-hexane system, thereby obtaining 3.34 g (32.0%) of one diastereomer of the title compound as a single compound (isomer) in the form of white crystals.

$^1$H-NMR (400 MHz, CDCl$_3$) δ0.34–0.35 (2H, m), 0.44–0.48 (1H, m), 0.58–0.65 (1H, m), 0.72–0.79 (1H, m), 1.44 (9H, s), 2.28 (1H, dd, J=17.09, 9.04 Hz), 2.44 (1H, dd, J=17.09, 8.44 Hz), 2.67–2.73 (1H, m), 3.04–3.06 (1H, m), 3.25–3.30 (1H, m), 3.47 (1H, t, J=8.79 Hz), 4.57 (1H, s), 5.84 (1H, s)

REFERENCE EXAMPLE 10

1-Benzyl-4-[1-(S)-tert-butoxycarbonylamino-1-cyclopropyl]methylpyrrolidin-2-one (isomer A)

Under a stream of nitrogen, 4-[1-(S)-tert-butoxycarbonylamino-1-cyclopropyl]methylpyrrolidin-2-one (3.15 g, 12.4 mmol) was dissolved in dry dimethylformamide (60 ml), and the solution was mixed with 60% oily sodium hydride (685 mg, 16.1 mmol) under ice-cooling. After 30 minutes of stirring at room temperature, this was mixed with benzyl bromide (2.04 ml, 16.1 mmol) under ice-cooling, and the mixture was stirred at room temperature for 13 hours. The reaction solution was mixed with water (200 ml) under ice-cooling and extracted with ethyl acetate (250 ml). The thus separated organic layer was washed with water (200 ml×2) and saturated sodium chloride aqueous solution (150 ml) in that order, and then dried over anhydrous magnesium sulfate. After filtration, the solvent was applied to a flash silica gel chromatography and eluted with n-hexane-ethyl acetate=1:1, thereby obtaining 2.74 g (64.2%) of the title compound as colorless amorphous.

$^1$H-NMR (400 MHz, CDCl$_3$) δ: 0.27–0.28 (2H, m), 0.39–0.43 (1H, m), 0.52–0.56 (1H, m), 0.66–0.72 (1H, m), 1.41 (9H, s), 2.39–2.42 (1H, m), 2.54–2.62 (2H, m), 3.01 (1H, s), 3.29–3.33 (1H, m), 4.40 (1H, s), 4.33, 4.55 (each 1 H, ABq, J=14.4 Hz), 7.23–7.36 (5H, m)

REFERENCE EXAMPLE 11

1-Benzyl-3-[1-(S)-tert-butoxycarbonylamino-1-cyclopropyl]methylpyrrolidine (isomer A)

Under a stream of nitrogen, 1-benzyl-4-[1-(S)-tert-butoxycarbonylamino-1-cyclopropyl]methylpyrrolidin-2-one (2.74 g, 7.95 mmol) was dissolved in dry tetrahydrofuran (70 ml) to which, under ice-cooling, was subsequently added dropwise a borane-tetrahydrofuran complex (1.0 N tetrahydrofuran solution; 47.7 ml, 47.7 mol). After completion of the dropwise addition, and the mixture was stirred at room temperature for 16 hours. The reaction solution was concentrated under a reduced pressure, mixed with a solution of ethanol:water=10:1 (130 ml) and triethylamine (20 ml), and then heated under reflux for 4 hours. The reaction solution was concentrated under a reduced pressure and mixed with chloroform (100 ml), and the thus separated organic layer was washed with water (100 ml) and saturated sodium chloride aqueous solution (50 ml) in that order, and then dried over anhydrous sodium sulfate. After filtration, the solvent was evaporated under a reduced pressure, and the thus obtained residue was applied to a flash silica gel chromatography and eluted with chloroform:methanol=95:5, thereby obtaining 2.63 g (100%) of the title compound as a colorless oil.

$^1$H-NMR (400 MHz, CDCl$_3$) δ0.19–0.23 (1H, m), 0.35–0.44 (3H, m), 0.73–0.76 (1H, m), 1.44 (9H, s), 1.60–1.66 (1H, m), 1.94–2.00 (1H, m), 2.36–2.42 (2H, m), 2.51–2.66 (3H, m), 2.95–3.02 (1H, m), 3.52, 3.67 (each 1 H, ABq, J=12.9 Hz), 4.58 (1H, s), 7.24–7.34 (5H, m)

REFERENCE EXAMPLE 12

1-Benzyloxycarbonyl-3-[1-(S)-tert-butoxycarbonylamino-1-cyclopropyl]methylpyrrolidine (isomer A=isomer F3 of Reference Example 3)

1-Benzyl-3-[1-(S)-tert-butoxycarbonylamino-1-cyclopropyl]methylpyrrolidine (isomer A; 238 mg, 0.720 mmol) was dissolved in dry dichloromethane (10 ml) to which was subsequently added dropwise benzyl chloroformate (309 4μl, 2.16 mmol) under ice-cooling. After 8 hours of stirring at room temperature, the reaction solution was concentrated under a reduced pressure. The resulting residue was applied to a flash silica gel chromatography and eluted with n-hexane:ethyl acetate=2:1, thereby obtaining 197 mg (73.1%) of the title compound as colorless amorphous.

The Rf value of TLC (thin layer chromatography, development with n-hexane:ethyl acetate=1:1) and $^1$H-NMR data (shown below) of this product coincided with those of the isomer F3 described in Reference Example 4. In addition, when this product was checked by HPLC analysis using a chiral column, its HPLC retention time coincided with the retention time of the optical isomer F3 described in reference Example 4. In consequence, it was confirmed that this product (isomer A) is the optical isomer F3 described in Reference Example 4.

$^1$H-NMR (400 MHz, CDCl$_3$) δ: 0.28–0.40 (2H, m), 0.41–0.45 (1H, m), 0.53–0.63 (1H, m), 0.72–0.81 (1H, m), 1.43 (9H, s), 1.67–1.79 (1H, m), 2.03–2.09 (1H, m), 2.37–2.40 (1H, m), 2.95–3.08 (1H, m), 3.16 (1H, t, J=10.74 Hz), 3.32–3.39 (1H, m), 3.54–3.69 (2H, m), 4.48 (1H, brs), 5.13 (2H, s), 7.31–7.37 (5H, m)

HPLC analysis conditions;
 Column: CHIRALPAKAD (Daicel Chemical Industries), 0.46 cm×25 cm
 Mobile phase: n-hexane:2-propanol=80:20 (v/v)
 Flow rate: 1.0 ml/min
 Temperature: room temperature
 Detection: UV (254 nm)
Retention time of isomer A (F3): 8.16 minutes
Optical purity: 99% e.e.

REFERENCE EXAMPLE 13

3-[1-(S)-tert-Butoxycarbonylamino-1-cyclopropyl]methylpyrrolidine (isomer A: F3)

1-Benzyl-3-[1-(S)-tert-butoxycarbonylamino-1-cyclopropyl]methylpyrrolidine (isomer A; 744 mg, 2.25 mmol) was dissolved in dry ethanol (30 ml), and the solution was mixed with 10% palladium on carbon catalyst (water content 50%; 750 mg) and stirred at 45° C. (external temperature) for 1 hour in an atmosphere of hydrogen under atmospheric pressure. The reaction solution was filtered through celite, and the resulting filtrate was concentrated under a reduced pressure, thereby obtaining 542 mg (quantitative) of the title compound as white crystals.

$^1$H-NMR (400 MHz, CDCl$_3$) δ: 0.27–0.42 (2H, m), 0.53–0.57 (1H, m), 0.74–0.81 (1H, m), 1.43 (9H, s), 1.55–1.60 (1H, m), 1.89–1.95 (1H, m), 2.23–2.26 (3H, m), 2.73–2.77 (1H, m), 2.85–2.90 (1H, m), 2.95–3.01 (2H, m)

INVENTIVE EXAMPLE 5

5-Amino-7-[3-[1-(S)-amino-1-cyclopropyl]methylpyrrolidin-1-yl]-6,8-difluoro-1-[2-(S)-fluoro-1-(R)-cyclopropyl]-1,4-dihydro-4-oxoquinoline-3-carboxylic acid (the substituent at the 7-position is originated from isomer A, F3)

3-[1-(S)-tert-Butoxycarbonylamino-1-cyclopropyl]methylpyrrolidine (isomer A: F3; 541 mg, 2.25 mmol) and triethylamine (6 ml) were added to dry acetonitrile (30 ml), and the mixture was further mixed with 5-amino-6,7,8-trifluoro-1-[2-(S)-fluoro-1-(R)-cyclopropyl]-1,4-dihydro-4- oxoquinoline-3-carboxylic acid (548 mg, 1.73 mmol) and heated under reflux for 15 hours. After cooling of the reaction solution, the thus precipitated crystals were collected by filtration, washed with acetonitrile, mixed with concentrated hydrochloric acid (15 ml) under ice-cooling and then stirred at room temperature for 5 minutes. This was mixed with distilled water (15 ml), and the thus obtained acidic aqueous solution was washed with dichloromethane (20 ml×3), adjusted to pH 11 with sodium hydroxide aqueous solution under ice-cooling and then washed with chloroform (30 ml). The resulting basic aqueous solution was adjusted to pH 7.4 with 1 N hydrochloric acid and extracted with chloroform (100 ml×5). After drying over anhydrous sodium sulfate, the solvent was evaporated under a reduced pressure. Thereafter, the resulting residue was purified by recrystallizing from an ethanol-28% aqueous ammonia and then dried under a reduced pressure, thereby obtaining 569 mg (75.3%) of the title compound as yellow needle crystals.

The Rf value of TLC (thin layer chromatography, developed with under layer chloroform:methanol:water=7:3:1) and $^1$H-NMR data (shown below) of this product coincided with the data described in Inventive Example 3.

$^1$H-NMR (400 MHz, 0.1 N NaOD) δ0.13–0.17 (1H, m), 0.21–0.29 (1H, m), 0.41–0.48 (1H, m), 0.51–0.61 (1H, m), 0.73–0.82 (1H, m), 1.43–1.53 (3H, m), 1.81 (1H, t, J=8.79 Hz), 2.10–2.27 (2H, m), 3.41–3.47 (1H, m), 3.49–3.58 (1H, m), 3.59–3.66 (1H, m), 3.73–3.81 (2H, m), 4.95 (1H, dm, J=65.11 Hz), 8.19 (1H, s)

Melting point: 192.5–194.5° C.

Elemental analysis data for $C_{21}H_{23}F_3N_4O_3 \cdot 0.25H_2O$ Calcd.: C, 57.20; H, 5.37; N, 12.71. Found: C, 57.18; H, 5.39; N, 12.78.

Specific rotation: $[\alpha]_D^{20}$=146.1° (c 0.32, 0.1 N NaOH)

INVENTIVE EXAMPLE 6

7-[3-[1-(S)-Amino-1-cyclopropyl]methylpyrrolidin-1-yl]-6-fluoro-1-[2-(S)-fluoro-1-(R)-cyclopropyl]-1,4-dihydro-8-methoxy-4-oxoquinoline-3-carboxylic acid (the substituent at the 7position is originated from isomer A, F3)

4-[1-(S)-tert-Butoxycarbonylamino-1-cyclopropyl]methylpyrrolidine (isomer A: F3; 240 mg, 1.00 mmol) and triethylamine (0.279 ml, 2.00 mmol) were added to dry dimethyl sulfoxide (1.5 ml). To this was further added 6,7-difluoro-1-[2-(S)-fluoro-1-(R)-cyclopropyl]-1,4-dihydro-8-methyl-4-oxoquinoline-3-carboxylic acid-$BF_2$ chelate (328 mg, 0.909 mmol), and the mixture was stirred at room temperature for 17 hours and then at 35° C. for 4 hours. After concentration of the reaction solution under a reduced pressure, the resulting residue was mixed with water, and the thus precipitated solid was collected by filtration and washed with water. The thus obtained solid was suspended in a solution of ethanol:water=10:1, and the suspension was mixed with triethylamine (2 ml) and heated under reflux for 3 hours. After cooling, the reaction solution was concentrated under a reduced pressure, and the resulting residue was dissolved in chloroform (100 ml). The organic layer was washed with 10% citric acid aqueous solution (50 ml) and then dried over anhydrous sodium sulfate. After filtration, the resulting filtrate was concentrated under a reduced pressure, concentrated hydrochloric acid (5 ml) was added dropwise to the thus obtained residue under ice-cooling and then the mixture was stirred at room temperature for 30 minutes. The reaction solution was mixed with 1 N hydrochloric acid (5 ml), the thus obtained yellow acidic aqueous solution was washed with chloroform (50 ml×5) and adjusted to pH 12.0 with sodium hydroxide aqueous solution, and then the insoluble material was removed by filtration. The resulting basic aqueous solution was adjusted to pH 7.4 with 1 N hydrochloric acid and extracted with chloroform (100 ml×4). After drying over anhydrous sodium sulfate, the solvent was evaporated under a reduced pressure. Thereafter, the resulting residue was purified by recrystallizing from ethanol and then dried under a reduced pressure, thereby obtaining 285 mg (67.3%) of the title compound as yellow crystals.

$^1$H-NMR (400 MHz, 0.1 N NaOD) δ0.01–0.05 (1H, m), 0.29–0.32 (1H, m), 0.39–0.40 (1H, m), 0.64–0.66 (1H, m), 1.15–1.22 (1H, m), 1.33–1.40 (1H, m), 1.43–1.54 (1H, m), 1.73–1.77 (1H, m), 1.96–1.98 (1H, m), 2.12–2.14 (1H, m), 3.28–3.51 (4H, m), 3.42 (3H, s), 3.81–3.86 (1H, m), 4.86 (1H, dm, J=66.6 Hz), 7.49 (1H, d, J=4.56 Hz), 8.25 (1H, d, J=3.42 Hz)

Melting point: 197.5–198.5° C.

Elemental analysis data for $C_{22}H_{25}F_2N_3O_4 \cdot 0.5H_2O \cdot 0.5EtOH$ Calcd.: C, 59.50; H, 6.28; N, 9.03. Found: C, 59.50; H, 6.39; N, 8.87.

Specific rotation: $[\alpha]_D^{20}$=−105.5° (c 0.88, 0.1 N NaOH)

INVENTIVE EXAMPLE 7

5-Amino-7-[3-[1-(S)-amino-1-cyclopropyl]methylpyrrolidin-1-yl]-6-fluoro-1-[2-(S)-fluoro-1-(R)-cyclopropyl]-1,4-dihydro-8-methyl-4-oxoquinoline-3-carboxylic acid (the substituent at the 7-position is originated from isomer A, F3)

4-[1-(S)-tert-Butoxycarbonylamino-1-cyclopropyl]methylpyrrolidine (481 mg, 2.00 mmol) and triethylamine (1.5 ml) were added to dry dimethyl sulfoxide (2 ml), and the mixture was further mixed with 5-amino-6,7-difluoro-1-[2-(S)-fluoro-1-(R)-cyclopropyl]-1,4-dihydro-8-methyl-4-oxoquinoline-3-carboxylic acid (416 mg, 1.33 mmol) and heated under reflux for 72 hours in an atmosphere of nitrogen. After concentration of the reaction solution under a reduced pressure, the resulting residue was dissolved in chloroform (100 ml). The organic layer was washed with 10% citric acid aqueous solution (50 ml) and then dried over anhydrous sodium sulfate. After filtration, the resulting filtrate was concentrated under a reduced pressure, concentrated hydrochloric acid (5 ml) was added dropwise to the thus obtained residue under ice-cooling and then the mixture was stirred at room temperature for 30 minutes. The reaction solution was mixed with 1 N hydrochloric acid (5 ml), the thus obtained yellow acidic aqueous solution was washed with chloroform (50 ml×5) and adjusted to pH 12.0 with sodium hydroxide aqueous solution, and then the insoluble material was removed by filtration. The resulting basic aqueous solution was adjusted to pH 7.4 with 1 N hydrochloric acid and extracted with chloroform (100 ml×3). After drying over anhydrous sodium sulfate, the solvent was evaporated under a reduced pressure. Thereafter, the resulting residue was purified by a preparative thin-layer chromatography (developed with under layer of chloroform:methanol:water=7:3:1), recrystallized from isopropyl alcohol and then dried under a reduced pressure, thereby obtaining 70.0 mg (12.1%) of the title compound as yellow crystals.

$^1$H-NMR (400 MHz, 0.1 N NaOD) δ0.01–0.10 (2H, m), 0.27–0.39 (2H, m), 0.58–0.64 (1H, m), 0.88–0.97 (1H, m), 1.33–1.45 (2H, m), 1.71–1.74 (1H, m), 1.97–2.10 (2H, m), 2.08 (3H, s), 3.01–3.05 (1H, m), 3.17–3.21 (1H, m), 3.34–3.38 (1H, m), 3.58–3.62 (1H, m), 3.75–3.79 (1H, m), 4.90 (1H, dm), 8.14 (1H, s)

Melting point: 226.7–227.9° C.

Elemental analysis data for $C_{22}H_{26}F_2N_4O_3$ Calcd.: C, 61.10; H, 6.06; N, 12.96. Found: C, 60.84; H, 6.07; N, 12.98. Specific rotation: $[\alpha]_D^{20}=-329.0°$ (c 0.20, 0.1 N NaOH)

INVENTIVE EXAMPLE 8

7-[3-[1-(S)-Amino-1-cyclopropyl)methylpyrrolidin-1-yl]-1-cyclopropyl-1,4-dihydro-8-methoxy-4-oxoquinoline-3-carboxylic acid (the substituent at the 7position is originated from isomer A, F3)

4-[1-(S)-tert-Butoxycarbonylamino-1-cyclopropyl]methylpyrrolidine (isomer A: F3; 330 mg, 1.37 mmol) and triethylamine (0.485 ml, 3.48 mmol) were added to 3.0 ml of dry dimethyl sulfoxide, and the mixture was further mixed with 6-fluoro-1-cyclopropyl-1,4-dihydro-8methoxy-4-oxoquinoline-3-carboxylic acid (321 mg, 1.16 mmol) and stirred at 100° C. for 15 hours. After concentration of the reaction solution under a reduced pressure, the resulting residue was dissolved in 100 ml of chloroform. The organic layer was washed with 50 ml of 10% citric acid aqueous solution and then dried over anhydrous sodium sulfate. After filtration, the resulting filtrate was concentrated under a reduced pressure, 5 ml of concentrated hydrochloric acid was added dropwise to the thus obtained residue under ice-cooling and then the mixture was stirred at room temperature for 30 minutes. The reaction solution was mixed with 5 ml of 1 N hydrochloric acid and the thus obtained yellow acidic aqueous solution was washed with chloroform (50 ml×4), the resulting insoluble material was removed by filtration, and then the solution was adjusted to pH 12.0 with sodium hydroxide aqueous solution. The resulting basic aqueous solution was adjusted to pH 7.4 with 1 N hydrochloric acid and extracted with chloroform (100 ml×4). After drying over anhydrous sodium sulfate, the solvent was evaporated under a reduced pressure. Thereafter, the resulting residue was purified by recrystallizing from ethanol-aqueous ammonia and then dried under a reduced pressure, thereby obtaining 230 mg (49.9%) of the title compound as yellow crystals.

1H-NMR (400 MHz, 0.1 N NaOD) δ: 0.17–0.18 (1H, m), 0.28–0.29 (1H, m), 0.46–0.47 (1H, m), 0.57–0.58 (1H, m), 0.77–0.79 (2H, m), 1.02–1.04 (2H, m), 1.17–1.21 (2H, m), 1.69–1.81 (1H, m), 1.92–1.95 (1H, m), 2.18–2.27 (1H, m), 2.35–2.40 (1H, m), 3.33–3.52 (3H, m), 3.52 (3H, s), 4.01–4.11 (1H, m), 7.03 (1H, d, J=8.79 Hz), 7.91 (1H, d, J=9.03 Hz), 8.48 (1H, s)

Melting point: 220–221° C.

Elemental analysis data for $C_{22}H_{27}N_3O_4 \cdot 0.5H_2O$ Calcd.: C, 65.74; H, 6.90; N, 10.45. Found: C, 65.96; H, 6.90; N, 10.36.

REFERENCE EXAMPLE 14

1-[1-(R)-Phenylethyl]-5-oxopyrrolidine-3-(R)-(N-methyl-N-methoxy)carboxamide

Oxalyl chloride (6.54 ml, 75.0 mmol) and dimethylformamide (3 drops) were added to dichloromethane solution (200 ml) of 1-[1-(R)-phenylethyl]-5-oxopyrrolidine-3-(R)-carboxylic acid (11.7 g, 50.0 mmol) under ice-cooling, and the mixture was stirred at room temperature for a whole day and night. After evaporation of the solvent under a reduced pressure, toluene (100 ml) was added to the resulting residue and then the solvent was again evaporated under a reduced pressure. The thus obtained residue was mixed with dichloromethane (200 ml) and N,O-ethylhydroxylamine hydrochloride (5.47 g, 55.5 mmol), and to the mixture, while stirring under ice-cooling, was then added dropwise dichloromethane solution (50 ml) of triethylamine (17.4 ml, 125 mmol) in 15 minutes. This was stirred under ice-cooling for 30 minutes and then at room temperature for 3 hours. The reaction solution was washed with 10% citric acid aqueous solution (100 ml), water (100 ml) and saturated sodium bicarbonate aqueous solution (100 ml) in that order and then dried over anhydrous sodium sulfate. The solvent was evaporated under a reduced pressure, and the resulting residue was applied to a silica gel column chromatography and eluted with a gradient of from chloroform:methanol=50:1 to 20:1, thereby obtaining 11.3 g (82%) of the title compound as a brown oil.

$^1$H-NMR (400 MHz, CDCl$_3$) δ: 1.54 (3H, d, J=6.84 Hz), 2.65 (1H, dd, J=9.77, 7.09 Hz), 2.77 (1H, dd, J=8.79, 7.09 Hz), 3.12–3.18 (1H, m), 3.20 (3H, s), 3.37–3.48 (1H, m), 3.55–3.64 (1H, m), 3.65 (3H, s), 5.50 (1H, q, J=6.84 Hz), 7.28–7.37 (5H, m)

REFERENCE EXAMPLE 15

4-(R)-Cyclobutylcarbonyl-1-[1-(R)-phenylethyl]-2-pyrrolidone

In an atmosphere of nitrogen, cyclobutylmagnesium chloride (1 N tetrahydrofuran solution, 28 ml) prepared from chlorocyclobutane was added dropwise to tetrahydrofuran solution (50 ml) of 1-[1-(R)-phenylethyl]-5-oxopyrrolidine-3-(R)-(N-methyl-N-methoxy)carboxamide (1.93 g, 7.00 mmol), and the mixture was stirred at room temperature for 30 minutes. The reaction solution was mixed with 1 N hydrochloric acid (50 ml) under ice-cooling and extracted with ethyl acetate (80 ml×2), and the organic layer was washed with saturated sodium chloride aqueous solution (100 ml) and then dried over anhydrous sodium sulfate. The solvent was evaporated under a reduced pressure, and the thus obtained residue was applied to a silica gel column chromatography and eluted with n-hexane:ethyl acetate=1:2, thereby obtaining 1.47 g (78%) of the title compound as a light yellow oil.

$^1$H-NMR (400 MHz, CDCl$_3$) δ: 1.53 (3H, d, J=7.33 Hz), 1.78–1.89 (1H, m), 1.92–2.06 (1H, m), 2.06–2.31 (4H, m), 2.58–2.65 (2H, m), 3.05 (1H, dd, J=9.28, 8.79 Hz), 3.13–3.21 (1H, m), 3.31 (1H, quint, J=8.30 Hz), 3.53 (1H, dd, J=9.28, 6.83 Hz), 5.48 (1H, q, J=7.33 Hz), 7.27–7.37 (5H, m)

REFERENCE EXAMPLE 16

4-(R)-(1-Cyclobutyl-1-hydroxy)methyl-1-[1-(R)-phenylethyl]-2-pyrrolidone

Under ice-cooling, sodium borohydride (295 mg) was added to ethanol (40 ml) solution of 4-(R)-cyclobutylcarbonyl-1-[1-(R)-phenylethyl]-2-pyrrolidone (2.12 g, 7.80 mol), and the mixture was stirred at the same temperature for 1 hour. The reaction solution was mixed with 10% citric acid (50 ml) under ice-cooling, ethanol was evaporated under a reduced pressure, the thus obtained residue was extracted with chloroform (80 ml×2), and then the organic layer was washed with saturated sodium chloride aqueous solution (100 ml) and dried over anhydrous sodium sulfate. The solvent was evaporated under a reduced pressure, and the thus obtained residue was applied to a silica gel column chromatography and eluted with a gradient of from n-hexane:ethyl acetate=1:3 to ethyl acetate, thereby obtaining 2.10 g (98%) of the title compound as a light yellow oil (isomer mixture).

$^1$H-NMR (400 MHz, CDCl$_3$) δ1.50 (3H, d, J=6.83 Hz), 1.68–2.01 (6H, m), 2.14–2.45 (3H, m), 2.45–2.56 (1H, m), 2.91–3.05 (1H, m), 3.19–3.31 (1H, m), 3.41–3.49 (1H, m), 5.42–5.49 (1H, m), 7.24–7.36 (5H, m)

REFERENCE EXAMPLE 17

4-(R)-(1-Azido-1-cyclobutyl)methyl-1-[1-(R)-phenylethyl]-2-pyrrolidone

Under ice-cooling, triethylamine (1.36 ml, 9.80 mmol) and then methanesulfonyl chloride (640 μl, 8.30 mmol) were added to dichloromethane (35 ml) solution of 4-(R)-(1-cyclobutyl-1-hydroxy)methyl-1-[1-(R)-phenylethyl]-2-pyrolidone (2.05 g, 7.50 mmol), and the mixture was stirred at the same temperature for 1 hour. The reaction solution was mixed with 10% citric acid (35 ml) under ice-cooling and extracted with chloroform (50 ml×2), and the organic layer was washed with saturated sodium chloride aqueous solution (150 ml) and then dried over anhydrous sodium sulfate. After evaporation of the solvent under a reduced pressure, the thus obtained residue was dissolved in N,N'-dimethylformamide (30 ml), and the solution was mixed with sodium azide (1.46 g, 22.5 mmol) and stirred at 60° C. for 3 hours. After cooling, the reaction solution was mixed with water (150 ml) under ice-cooling and extracted with ethyl acetate (150 ml×3), and the organic layer was washed with saturated sodium chloride aqueous solution (150 ml) and then dried over anhydrous sodium sulfate. After evaporation of the solvent under a reduced pressure, the thus obtained residue was applied to a silica gel column chromatography and eluted with n-hexane:ethyl acetate=3:2, thereby obtaining 898 mg (40%) of a low polarity title compound (isomer B1) as a colorless oil and then with n-hexane:ethyl acetate=2:3, thereby obtaining 847 mg (38%) of a high polarity title compound (isomer B2) as colorless crystals.

Isomer B1

$^1$H-NMR (400 MHz, CDCl$_3$) δ: 1.52 (3H, d, J=6.83 Hz), 1.72–2.01 (5H, m), 2.07–2.17 (1H, m), 2.26–2.41 (3H, m), 2.45–2.56 (1H, m), 2.98 (1H, dd, J=9.77, 7.81 Hz), 3.14 (1H, dd, J=9.77, 7.32 Hz), 3.32 (1H, dd, J=8.76, 3.91 Hz), 5.47 (1H, q, J=6.83 Hz), 7.25–7.35 (5H, m)

Isomer B2

$^1$H-NMR (400 MHz, CDCl$_3$) δ: 1.52 (3H, d, J=6.83 Hz), 1.75–2.03 (5H, m), 2.03–2.17 (1H, m), 2.19–2.38 (2H, m), 2.40–2.56 (2H, m), 2.99 (1H, dd, J=9.77, 8.30 Hz), 3.14 (1H, dd, J=9.77, 7.32 Hz), 3.30 (1H, dd, J=8.30, 6.34 Hz), 5.47 (1H, q, J=6.83 Hz), 7.25–7.35 (5H, m)

REFERENCE EXAMPLE 18

4-(R)-[1-(tert-Butoxycarbonyl)amino-1-cyclobutyl]methyl-1-[1-(R)-phenylethyl]-2-pyrrolidone (isomer B1)

Ethanol (50 ml) solution of 4-(R)-(1-azido-1-cyclobutyl)methyl-1-[1-(R)-phenylethyl]-2pyrrolidone (isomer B1) (835 mg, 2.80 mmol) was mixed with 10% palladium on carbon catalyst (water content 53.8%, 850 mg), and 5 hours of catalytic hydrogenation was carried out at room temperature in an atmosphere of hydrogen under atmospheric pressure. The reaction solution was filtered and the solvent was evaporated under a reduced pressure. The resulting residue was dissolved in dichloromethane (20 ml), and the solution was mixed with di-tert-butyl bicarbonate (917 mg) and triethylamine (780 1) and stirred at room temperature for 15 hours. The reaction solution was mixed with chloroform (50 ml) and washed with 10% citric acid (80 ml) and water (80 ml) and then the organic layer was dried over anhydrous sodium sulfate. The solvent was evaporated under a reduced pressure, and the thus obtained residue was applied to a silica gel column chromatography and eluted with a gradient of n-hexane:ethyl acetate=3:2 to 1:1, thereby obtaining 809 mg (78%) of the title compound as white amorphous.

$^1$H-NMR (400 MHz, CDCl$_3$) δ1.44 (9H, s), 1.48 (3H, d, J=7.32 Hz), 1.66–1.98 (6H, m), 2.17–2.43 (4H, m), 2.94–3.03 (1H, m), 3.09–3.18 (1H, m), 3.59–3.68 (1H, m), 4.46–4.58 (1H, m), 5.46 (1H, q, J=7.32 Hz), 7.27–7.35 (5H, m)

REFERENCE EXAMPLE 19

4-(R)-[1-(tert-Butoxycarbonyl)amino-1-cyclobutyl]methyl-1-[1-(R)-phenylethyl]-2-pyrrolidone (isomer B2)

Ethanol (40 ml) solution of 4-(R)-(1-azido-1-cyclobutyl)methyl-1-[1-(R)-phenylethyl]-2-pyrrolidone (isomer B2) (776 mg, 2.60 mmol) was mixed with 10% palladium on carbon catalyst (water content 53.8%, 800 mg) and 5 hours of catalytic hydrogenation was carried out at room temperature in an atmosphere of hydrogen under atmospheric pressure. The reaction solution was filtered and the solvent was evaporated under a reduced pressure. The thus obtained residue was dissolved in dichloromethane (20 ml), and the solution was mixed with di-tert-butyl bicarbonate (851 mg) and triethylamine (725 μl) and stirred at room temperature for 15 hours. The reaction solution was mixed with chloroform (50 ml) and washed with 10% citric acid (80 ml) and water (80 ml) and then the organic layer was dried over anhydrous sodium sulfate. The solvent was evaporated under a reduced pressure, and the thus obtained residue was applied to a silica gel column chromatography and eluted with a gradient of n-hexane:ethyl acetate=1:1 to 2:3, thereby obtaining 846 mg (87%) of the title compound as, white amorphous.

$^1$H-NMR (400 MHz, CDCl$_3$) δ: 1.43 (9H, s), 1.50 (3H, d, J=7.32 Hz), 1.70–1.96 (6H, m), 2.08–2.22 (1H, m), 2.22–2.36 (2H, m), 2.36–2.47 (1H, m), 2.96 (1H, dd, J=9.27, 8.30 Hz), 3.10 (1H, dd, J=,9.27, 8.79 Hz), 3.55–3.62 (1H, m), 4.28 (1H, d, J=9.77 Hz), 5.46 (1H, q, J=7.32 Hz), 7.25–7.35 (5H, m)

REFERENCE EXAMPLE 20

3-(R)-[1-(tert-Butoxycarbonyl)amino-1-cyclobutyl]methyl-1-[1-(R)-phenylethyl]pyrrolidine (isomer B1)

In an atmosphere of nitrogen, 1 M borane-tetrahydrofuran complex solution (5.6 ml) was added dropwise to tetrahydrofuran solution (15 ml) of 4-(R)-[1-(tert-butoxycarbonyl)amino-1-cyclobutyl]methyl-1-[1-(R)-phenylethyl]-2pyrrolidone (isomer B1) (700 mg, 1.88 mmol) under ice-cooling, and the mixture was stirred at room temperature for 13 hours. The solvent was evaporated under a reduced pressure, and the resulting residue was mixed with 80% aqueous ethanol (15 ml) and triethylamine (3 ml) and heated under reflux for 4 hours. After cooling, the solvent was evaporated under a reduced pressure, and the thus obtained residue was mixed with chloroform (30 ml), washed with water (10 ml) and saturated sodium chloride aqueous solution (10 ml) and then dried over anhydrous sodium sulfate. The solvent was evaporated under a reduced pressure, and the thus obtained residue was applied to a silica gel column chromatography and eluted with chloroform:methanol= 20:1, thereby obtaining 565 mg (84%) of the title compound as colorless crystals.

$^1$H-NMR (400 MHz, CDCl$_3$) δ1.36 (3H, d, J=6.84 Hz), 1.45 (9H, s), 1.66–1.95 (7H, m), 2.05–2.22 (2H, m), 2.22–2.34 (1H, m), 2.34–2.45 (2H, m), 3.15 (1H, q, J=6.84 Hz), 3.43–3.53 (1H, m), 4.54–4.62 (1H, m), 7.21–7.31 (5H, m)

REFERENCE EXAMPLE 21

3-(R)-[1-(tert-Butoxycarbonyl)amino-1-cyclobutyl] methyl-1-1-(R)-phenylethyl pyrrolidine (isomer B2)

In an atmosphere of nitrogen, 1 M borane-tetrahydrofuran complex solution (6.4 ml) was added dropwise to tetrahydrofuran solution (15 ml) of 4-(R)-[1-(tert-butoxycarbonyl) amino-1-cyclobutyl]methyl-1-[1-(R)-phenylethyl]-2pyrrolidone (isomer B2) (797 mg, 2.14 mmol) under ice-cooling, and the mixture was stirred at room temperature for 13 hours. The solvent was evaporated under a reduced pressure, and the resulting residue was mixed with 80% aqueous ethanol (15 ml) and triethylamine (3 ml) and heated under reflux for 4 hours. After cooling, the solvent was evaporated under a reduced pressure, and the thus obtained residue was mixed with chloroform (30 ml), washed with water (10 ml) and saturated sodium chloride aqueous solution (10 ml) and then dried over anhydrous sodium sulfate. The solvent was evaporated under a reduced pressure, and the thus obtained residue was applied to a silica gel column chromatography and eluted with chloroform:methanol= 20:1, thereby obtaining 743 mg (97%) of the title compound as colorless oil.

$^1$H-NMR (400 MHz, CDCl$_3$) δ: 1.37 (3H, d, J=6.83 Hz), 1.46 (9H, s), 1.64–1.93 (8H, m), 2.10–2.30 (3H, m), 2.30–2.51 (1H, m), 2.51–2.69 (2H, m), 3.11–3.23 (1H, m), 3.43–3.52 (1H, m), 4.92–5.01 (1H, m), 7.22–7.32 (5H, m)

REFERENCE EXAMPLE 22

3-(R)-[1-(tert-Butoxycarbonyl)amino-1-cyclobutyl] methylpyrrolidine (isomer B1)

10% Palladium on carbon catalyst (water content 53.8%, 500 mg) was added to ethanol (30 ml) solution of 3-(R)-[1-(tert-butoxycarbonyl)amino-1-cyclobutyl]methyl-1-[1-(R)-phenylethyl]pyrrolidine (isomer B1) (516 mg, 1.44 mmol), and the mixture was subjected to 5 hours of catalytic hydrogenation at an external temperature of 50C in an atmosphere of hydrogen under atmospheric pressure. The reaction solution was filtered and the solvent was evaporated under a reduced pressure, thereby obtaining 366 mg (quantitative) of the title compound as colorless crystals. This product was used in the subsequent reaction without purification.

REFERENCE EXAMPLE 23

3-(R)-[1-(tert-Butoxycarbonyl)amino-1-cyclobutyl] methylpyrrolidine (isomer B2)

10% Palladium on carbon catalyst (water content 53.8%, 650 mg) was added to ethanol (40 ml) solution of 3-(R)-[1-(tert-butoxycarbonyl)amino-1-cyclobutyl]methyl-1-[1-(R)-phenylethyl]pyrrolidine (isomer B2) (645 mg, 1.80 mmol), and the mixture was subjected to 5 hours of catalytic hydrogenation at an external temperature of 50° C. in an atmosphere of hydrogen under atmospheric pressure. The reaction solution was filtered and the solvent was evaporated under a reduced pressure, thereby obtaining 458 mg (quantitative) of the title compound as colorless crystals. This product was used in the subsequent reaction without purification.

INVENTIVE EXAMPLE 9

5-Amino-7-[3-(R)-(1-amino-1-cyclobutyl)methyl] pyrrolidin-1-yl]-6,8-difluoro-1-[2-(S)-fluoro-1-(R)-cyclopropyl]-1,4-dihydro-4oxoquinoline-3-carboxylic acid (the substituent at the 7-position is originated from B1)

5-Amino-6,7,8-trifluoro-1-[2-(S)-fluoro-1-(R)-cyclopropyl]-1,4-dihydro-4-oxoquinoline-3-carboxylic acid (379 mg, 1.20 mmol), 3-(R)-[1-(tert-butoxycarbonyl)amino-1-cyclobutyl]methylpyrrolidine (isomer B1) (366 mg, 1.44 mmol) and triethylamine (3 ml) were added to acetonitrile (15 ml) and heated under reflux for 8 hours. After cooling, the reaction solution was concentrated under a reduced pressure, and the thus obtained residue was mixed with concentrated hydrochloric acid (15 ml) under ice-cooling and then stirred at room temperature for 10 minutes. This hydrochloric acid solution was washed with chloroform (20 ml×3), and was made alkaline by adding 30% sodium hydroxide aqueous solution under ice-cooling and then stirred at room temperature for 1 hour. This suspension was adjusted to pH 7.6 by adding concentrated hydrochloric acid and 1 N hydrochloric acid and then extracted with chloroform (100 ml×3). The organic layer was dried over anhydrous sodium sulfate and the solvent was evaporated under a reduced pressure. Thereafter, the resulting residue was purified by recrystallizing from ethanol-n-hexane and then dried under a reduced pressure, thereby obtaining 386 mg (74%) of the title compound as light yellow crystals.

$^1$H-NMR (400 MHz, 0.1 N NaOD) δ: 1.22–1.83 (11H, m), 1.83–1.97 (1H, m), 1.97–2.18 (2H, m), 2.18–2.29 (1H, m), 3.07–3.28 (2H, m), 3.35–3.46 (1H, m), 3.53–3.69 (2H, m), 4.78–4.89 (0.5H, m), 4.93–5.02 (0.5H, m), 8.17 (1H, s)

Melting point: 175.3–177.6° C. (decomp.)

Elemental analysis data for $C_{22}H_{25}F3N_{4O3}$ Calcd.: C, 58.66; H, 5.59; N, 12.44. Found: C, 58.55; H, 5.61; N, 12.33.

INVENTIVE EXAMPLE 10

5-Amino-7-[3-(R)-(1-amino-1-cyclobutyl)methyl] pyrrolidin-1-yl]-6,8-difluoro-1-[2-(S)-fluoro-1-(R)-cyclopropyl] -1,4-dihydro-4-oxoquinoline-3-carboxylic acid (the substituent at the 7-position is originated from B2)

5-Amino-6,7,8-trifluoro-1-[2-(S)-fluoro-1-(R)-cyclopropyl]-1,4-dihydro-4-oxoquinoline-3-carboxylic acid (474 mg, 1.50 mmol), 3-(R)-[1-(tert-butoxycarbonyl)amino-1-cyclobutyl]methylpyrrolidine (isomer B2) (458 mg, 1.80 mmol) and triethylamine (4 ml) were added to acetonitrile (20 ml) and heated under reflux for 8 hours. After cooling, the reaction solution was concentrated under a reduced pressure, and the thus obtained residue was mixed with concentrated hydrochloric acid (15 ml) under ice-cooling and then stirred at room temperature for 10 minutes. This hydrochloric acid solution was washed with chloroform (20 ml×3), and was made alkaline by adding 30% sodium hydroxide aqueous solution under ice-cooling and then stirred at room temperature for 1 hour. This suspension was adjusted to pH 7.6 by adding concentrated hydrochloric acid and 1 N hydrochloric acid and then extracted with chloroform (100 ml×3). The organic layer was dried over anhydrous sodium sulfate and the solvent was evaporated under a reduced pressure. Thereafter, the resulting residue was purified by recrystallizing from chloroform-n-hexane and then dried under a reduced pressure, thereby obtaining 386 mg (74%) of the title compound as light yellow crystals.

$^1$H-NMR (400 MHz, 0.1 N NaOD) δ: 1.27–1.76 (7H, m), 1.76–1.99 (6H, m), 2.17–2.28 (1H, m), 2.34–2.42 (1H, m), 3.36–3.50 (2H, m), 3.50–3.59 (1H, m), 3.64–3.79 (2H, m), 4.79–4.89 (0.5H, m), 4.98–5.06 (0.5H, m), 8.19 (1H, s)

Melting point: 198.2–201.4° C. (decomp.)

Elemental analysis data for $C_{22}H_{25}F_3N_4O_3 \cdot 1.0H_2O$.
Calcd.: C, 56.40; H, 5.81; N, 11.96.

Found: C, 56.34; H, 5.84; N, 11.75.

The antibacterial activity of each compound of the present invention was measured in accordance with the standard method specified by the Japan Society of Chemotherapy, with the results shown in the following Table 2 as MIC values (μg/ml). In this connection, MIC values of levofloxacin (LVFX) and ciprofloxacin (CPEX) are also shown for the sake of comparison with the MIC values of the compounds of the present invention.

TABLE 2

| Strains | Compounds (Inventive Example No.) | | | |
|---|---|---|---|---|
| | 1 | 2 | 4 | 5 |
| E. coli, NIHJ | 0.006 | 0.013 | ≦0.003 | ≦0.003 |
| S. flexneri, 2A 5503 | 0.025 | 0.05 | ≦0.003 | ≦0.003 |
| Pr. vulgaris, 08601 | 0.2 | 0.1 | 0.05 | 0.013 |
| K. pneumoniae TYPE 1 | 0.1 | 0.1 | 0.025 | 0.013 |
| Ser. marcescens, 10100 | 0.2 | 0.2 | 0.05 | 0.025 |
| Ps. aeruginosa, 32104 | 0.39 | 0.78 | 0.1 | 0.05 |
| PS. aeruginosa, 32121 | 0.2 | 0.2 | 0.05 | 0.025 |
| X. maltophilia, IID 1275 | 0.39 | 0.39 | 0.05 | 0.05 |
| S. aureus, FDA 209P | 0.025 | 0.025 | ≦0.003 | ≦0.003 |
| S. epidermidis, 56500 | 0.1 | 0.1 | ≦0.003 | ≦0.003 |
| Str. pyogenes, G-36 | 0.39 | 0.2 | ≦0.003 | ≦0.003 |
| E. faecalis, ATCC 19433 | 0.2 | 0.2 | 0.025 | 0.013 |
| S. aureus, 870307 | 3.13 | 3.13 | 0.05 | 0.025 |
| Str. pneumoniae, J24 | 0.1 | 0.1 | ≦0.003 | ≦0.003 |

| Strains | Compounds (Inventive Example No.) | | | |
|---|---|---|---|---|
| | 6 | 7 | 8 | 9 |
| E. coli, NIHJ | ≦0.003 | ≦0.003 | 0.006 | ≦0.003 |
| S. flexneri, 2A 5503 | 0.006 | ≦0.003 | 0.1 | 0.005 |
| Pr. vulgaris, 08601 | 0.013 | 0.013 | 0.05 | 0.1 |
| K. pneumoniae TYPE 1 | 0.05 | 0.025 | 0.1 | 0.025 |
| Ser. marcescens, 10100 | 0.1 | 0.05 | 0.2 | 0.1 |
| Ps. aeruginosa, 32104 | 0.1 | 0.05 | 0.39 | 0.2 |
| PS. aeruginosa, 32121 | 0.05 | 0.025 | 0.2 | 0.1 |
| X. maltophilia, IID 1275 | 0.2 | 0.05 | 0.2 | 0.1 |
| S. aureus, FDA 209P | ≦0.003 | ≦0.003 | 0.006 | ≦0.003 |
| S. epidermidis, 56500 | 0.006 | ≦0.003 | 0.025 | ≦0.003 |
| Str. pyogenes, G-36 | ≦0.003 | ≦0.003 | 0.013 | 0.013 |
| E. faecalis, ATCC 19433 | 0.025 | 0.013 | 0.05 | 0.05 |
| S. aureus, 870307 | 0.1 | 0.025 | 0.2 | 0.10 |
| Str. pneumoniae, J24 | ≦0.003 | ≦0.003 | 0.006 | 0.006 |

| Strains | Compounds (Inventive Example No.) | | |
|---|---|---|---|
| | 10 | LVFX | CPFX |
| E. coli, NIHJ | ≦0.003 | 0.013 | ≦0.003 |
| S. flexneri, 2A 5503 | ≦0.003 | 0.025 | 0.006 |
| Pr. vulgaris, 08601 | 0.05 | 0.13 | ≦0.003 |
| K. pneumoniae TYPE 1 | 0.025 | 0.1 | 0.025 |
| Ser. marcescens, 10100 | 0.05 | 0.1 | 0.025 |

TABLE 2-continued

| Ps. aeruginosa, 32104 | 0.2 | 0.2 | 0.05 |
|---|---|---|---|
| PS. aeruginosa, 32121 | 0.2 | 0.1 | 0.025 |
| X. maltophilia, IID 1275 | 0.05 | 0.39 | 0.78 |
| S. aureus, FDA 209P | ≦0.003 | 0.2 | 0.1 |
| S. epidermidis, 56500 | ≦0.003 | 0.39 | 0.2 |
| Str. pyogenes, G-36 | ≦0.003 | 0.2 | 1.56 |
| E. faecalis, ATCC 19433 | 0.013 | 0.78 | 0.78 |
| S. aureus, 870307 | 0.05 | >6.25 | 3.13 |
| Str. pneumoniae, J24 | ≦0.003 | 0.78 | 0.1 |

INDUSTRIAL APPLICABILITY

The compound of the present invention is possessed of excellent antibacterial action against a broad range of Gram-negative and Gram-positive bacteria, particularly showing strong antibacterial activity against methicillin-resistant *Stapylococcus aureus,* penicillin-resistant pneumococcus, enterocuccus and the like Gram-positive bacteria and quinolone-resistant bacteria, and is also possessed of excellent safety and good pharmacokinetics, such as attenuation of micronuclear test, so that it is useful as an antibacterial compound to be used in the chemotherapy of bacterial infections.

What is claimed is:

1. A compound represented by the following formula (I) its salts and hydrates thereof:

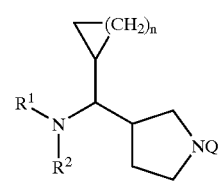

(I)

wherein $R^1$ and $R^2$ each independently represents a hydrogen atom or an alkyl group having 1 to 6 carbon atoms, in which the alkyl group may have one or more substituents selected from the group consisting of hydroxyl group, a halogen atom, an alkylthio group having 1 to 6 carbon atoms and an alkyloxy group; n is an integer of 1 to 4; and Q is a partial structure represented by the following formula (Ia):

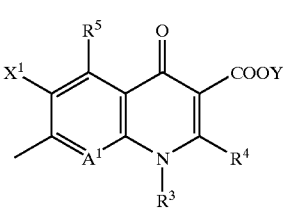

(Ia)

wherein $R^3$ represents an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms which may have a substituent, with the proviso that when R3 is a cyclopropyl group it is substituted by a halogen compound an aryl group which may have a substituent, a heteroaryl group which may have a substituent, an alkoxyl group having 1 to 6 carbon atoms or an alkylamino group having 1 to 6 carbon atoms;

R⁴ represents a hydrogen atom or an alkylthio group having 1 to 6 carbon atoms;

R⁴ and R³ may form together with a part of the mother skeleton a ring structure optionally containing a sulfur atom as a ring constituting atom thereof and optionally having an alkyl group having 1 to 6 carbon atoms as a substituent;

R⁵ represents a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, in which the amino group may have one or more substituents selected from the group consisting of a formyl group, an alkyl group having 1 to 6 carbon atoms and an acyl group having 2 to 5 carbon atoms;

X¹ represents a halogen atom or a hydrogen atom;

A¹ represents a nitrogen atom or a partial structure represented by formula (II):

(II)

wherein X² represents a hydrogen atom, an amino group, a halogen atom, a cyano group, a halogenomethyl group, a halogenamethoxyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, in which the amino group may have one or more substituents selected from the group consisting of a formyl group, an alkyl group having 1 to 6 carbon atoms and an acyl group having 2 to 5 carbon atoms; and X² and R³ may form together with a part of the mother skeleton a ring structure optionally containing an oxygen atom, a nitrogen atom or sulfur atom as a ring constituting atom thereof and optionally having an alkyl group having 1 to 6 carbon atoms as a substituent; and Y represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms or a phenylalkyl group composed of an alkylene group having 1 to 6 carbon atoms and a phenyl group.

2. A compound, its salts and hydrates thereof according to claim 1, wherein Q in the formula (I) is a 6-carboxy-9-fluoro-2,3-dihydro-3-(S)-methyl-7-oxo-7H-pyrido[1,2,3-de][1.4]benzoxazin-10-yl group.

3. A compound, its salts and hydrates thereof according to claim 1, wherein the compound of formula (I) is a stereochemically pure compound.

4. A compound, its salts and hydrates thereof according to claim 1, wherein R³ in the formula (I) is a halogenocyclopropyl group.

5. A compound, its salts and hydrates thereof according to claim 1, wherein the halogenocyclopropyl group in the formula (I) is a 1,2-cis-halogenocyclopropyl group.

6. A compound, its salts and hydrates thereof according to claim 5, wherein the halogenocyclopropyl group in the formula (I) is a stereochemically pure substituent.

7. A compound, its salts and hydrates thereof according to claim 6, wherein the halogenocyclopropyl group in the formula (I) is a (1R,2S)-2-halogenocyclopropyl group.

8. A compound, its salts and hydrates thereof according to claim 7, wherein the halogen atom of the halogenocyclopropyl group in the formula (I) is a fluorine atom.

9. A compound, its salts and hydrates thereof according to claim 8, wherein the compound of formula (I) is a stereochemically pure compound.

10. A compound, its salts and hydrates thereof according to claim 1, wherein n in the formula (I) is 1.

11. A compound, its salts and hydrates thereof according to claim 10, wherein the compound of formula (I) is a stereochemically pure compound.

12. 7-[3-[1-(S)-Amino-1-cyclopropyl]methylpyrrolidin-1-yl]-6-fluoro-1-[2-(S)-fluoro-1-(R)-cyclopropyl]-1,4-dihydro-8-methoxy-4-oxoquinoline-3-carboxylic acid, its salts and hydrates thereof.

13. 5-Amino-7-[3-[1-(S)-amino-1-cyclopropyl]methylpyrrolidin-1-yl]-6-fluoro-1-[2-(S)-fluoro-1-(R)-cyclopropyl]-1,4-dihydro-8-methyl-4-oxoquinoline-3-carboxylic acid, its salts and hydrates thereof.

14. 5-Amino-7-[3-[1-(S)-amino-1-cyclopropyl]methylpyrrolidin-1-yl]-6,8-difluoro-1-[2-(S)-fluoro-1-(R)-cyclopropyl]-1,4-dihydro-4-oxoquinoline-3-carboxylic acid, its salts and hydrates thereof.

15. A compound, its salts and hydrates thereof according to claim 1, wherein Y is a hydrogen atom.

16. A drug containing the compound, its salts and hydrates thereof described in any one of claims 1 to 15 as an active ingredient and a pharmaceutically acceptable carrier.

17. An antibacterial containing the compound, its salts and hydrates thereof described in any one of claims 1 to 15 as an active ingredient and a pharmaceutically acceptable carrier.

* * * * *